United States Patent [19]

Meanwell

[11] Patent Number: 5,262,540
[45] Date of Patent: Nov. 16, 1993

[54] [2(4,5-DIARYL-2 OXAZOYL SUBSTITUTED PHENOXY ALKANOIC ACID AND ESTERS

[75] Inventor: Nicholas A. Meanwell, East Hampton, Conn.

[73] Assignee: Bristol-Myers Squibb Company, New York, N.Y.

[21] Appl. No.: 59,519

[22] Filed: May 10, 1993

Related U.S. Application Data

[63] Continuation of Ser. No. 809,100, Dec. 11, 1991, abandoned, which is a continuation of Ser. No. 580,021, Sep. 10, 1990, abandoned, which is a continuation-in-part of Ser. No. 453,548, Dec. 20, 1989, abandoned.

[51] Int. Cl.$^5$ .............................................. A61K 31/42
[52] U.S. Cl. ................................. 514/374; 514/376; 548/110; 548/117; 548/235; 548/236
[58] Field of Search ................... 514/374; 548/235, 236

[56] References Cited

U.S. PATENT DOCUMENTS

| | | | |
|---|---|---|---|
| 3,578,671 | 5/1971 | Brown et al. | 514/374 |
| 4,391,814 | 7/1983 | Vorbrüggen | 514/365 |
| 4,460,598 | 7/1984 | Lautenschlager et al. | 548/336 |
| 4,735,961 | 4/1988 | Baldwin et al. | 514/374 |
| 4,775,674 | 10/1988 | Meanwell et al. | 514/253 |
| 4,826,990 | 5/1989 | Musser et al. | 548/235 |
| 4,925,861 | 5/1990 | Hayashi et al. | 514/365 |
| 5,187,188 | 2/1993 | Meanwell | 514/374 |

FOREIGN PATENT DOCUMENTS

| | | | |
|---|---|---|---|
| 0318085 | 5/1989 | European Pat. Off. | 548/236 |
| 2110363 | 9/1971 | Fed. Rep. of Germany | 514/374 |

OTHER PUBLICATIONS

Aldous et al. J. Org. Chem., 25:1151 (1960).
Pridgen et al., Tetrahedron Lett. vol. 25, No. 7, pp. 2835-2838 (1984).
Brown et al. Nature vol. 219, Jul. 13, 1966 p. 164.
Meanwell et al. J. Med Chem. 35 389-97 (1992).
Meanwell et al. J. Med. Chem. 35 3483-97 (1992).
Meanwell et al. J. Med. Chem. 35 3498-3512 (1992).

Primary Examiner—Donald G. Daus
Attorney, Agent, or Firm—Robert H. Uloth; Michelle A. Kaye

[57] ABSTRACT

Oxazole derivatives having Formula I or II are disclosed which are useful as inhibitors of mammalian blood platelet aggregation.

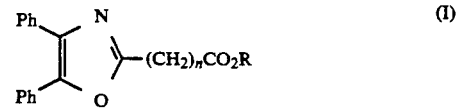

(I)

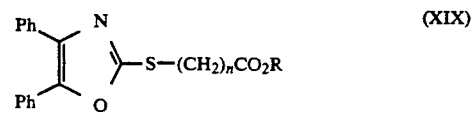

(XIX)

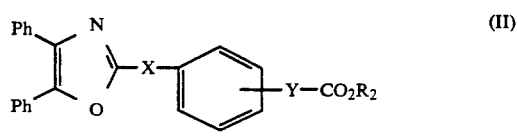

(II)

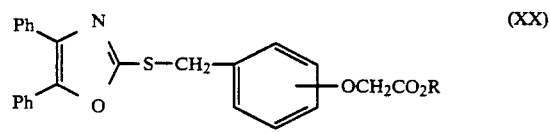

(XX)

Formula I and Formula XIX compounds are those wherein n is 7-9 and R is hydrogen or lower alkyl. Formula II compounds are those wherein R is hydrogen, lower alkyl or together with $CO_2$ is tetrazol-1-yl; $R_1$ is phenyl or thienyl; X is a divalent connecting group selected from the group consisting of $CH_2CH_2$, $CH=CH$, and $CH_2O$; Y is a divalent connecting group attached to the 3 or 4 phenyl position selected from the group consisting of $OCH_2$, $CH_2CH_2$ and $CH=CH$. Formula XX compounds are those wherein the $OCH_2CO_2R$ moiety is attached to the 3 or 4 phenyl position and R is hydrogen or lower alkyl.

34 Claims, No Drawings

[2(4,5-DIARYL-2 OXAZOYL SUBSTITUTED PHENOXY ALKANOIC ACID AND ESTERS

CROSS REFERENCE TO RELATED APPLICATIONS

This application is a continuation of application Ser. No. 07/809,100, filed Dec. 11, 1991, now abandoned, which is a continuation of application Ser. No. 07/580,021 filed Sep. 10, 1990, also abandoned which is a CIP of Ser. No. 07/453,548 filed Dec. 20, 1989, abandoned.

BACKGROUND OF THE INVENTION

This invention generally pertains to heterocyclic carbon compounds having drug and bioaffecting properties and to their preparation and use. In particular, the invention is concerned with oxazole derivatives characterized by Formulas I and II, infra., which are inhibitors of blood platelet aggregation.

The following chemical literature and patents are illustrative of related oxazole prior art known to applicant.

D. L. Aldous, et al., *J. Org. Chem.*, 25, 1151 (1960) describe the chemistry of styryloxazoles of the formula

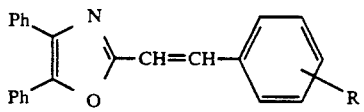

wherein R is hydrogen, p-methoxy, o-hydroxy and 3,4-methylendioxy.

Brown, U.S. Pat. No. 3,578,671 describes a class of oxazole-2-polycarbon aliphatic monocarboxylic acids arylated at the 4- and/or 5-position in the oxazole ring of the formula

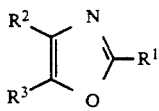

in which each of the substituents $R^2$ and $R^3$ is a member of the group consisting of unsubstituted phenyl, naphthyl, thienyl and furyl radicals and phenyl radicals substituted by substituents selected from the group consisting of halogen, lower alkyl, lower alkoxy, nitro and trifluoromethyl radicals; and wherein $R^1$ is selected from the group consisting of carboxyalkyl- and carboxylalkenyl radicals each containing from 2 to 5 carbon atoms and the amides, hydroxamic acid derivatives, lower alkyl esters and lower alkanoyloxy-lower-alkyl esters thereof. The compounds of U.S. Pat. No. 3,578,671 include the clinically effective anti-inflammatory agent known generically as oxaprozin ($R^2 = R^3 = $ phenyl, $R^1 = (CH_2)_2CO_2H$).

Meanwell, et al., U.S. Pat. No. 4,775,674 describe a series of 2,3-dihydro-2-oxo-1H-imidazo[4,5-quinolinyl] ether derivatives of the formula

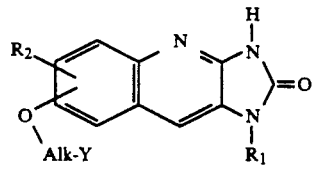

wherein inter alia $R_1$ and $R_2$ are hydrogen, and "alk-Y" an alkanoic acid and ester residue. The compounds of U.S. Pat. No. 4,701,459 have cyclic AMP phosphodiesterase inhibitor activity and are useful as inhibitors of blood platelet aggregation and/or as cardiotonic agents.

Lautenschlager, et al., U.S. Pat. No. 4,460,598 issued Jul. 17, 1984 describe a series of triphenylis imidazol-2-yloxyalkanoic acids having the formula

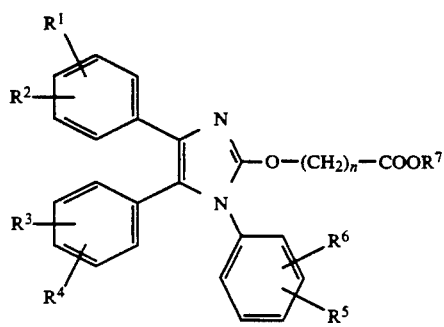

wherein $R^1$, $R^2$, $R^3$, $R^4$, $R^5$ and $R^6$ each are H, halogen, alkyl, alkoxy and trifluoromethyl; n is an integer of 1 to 10 and $R^7$ is H, alkali metal ions, alkyl or benzyl group. The compounds of U.S. Pat. No. 4,460,598 are reportedly useful in the treatment of thromboembolic, inflammatory and/or atherosclerotic disease in man. A particularly preferred member of the series wherein $R^1$ to $R^6$ is hydrogen, n is 7 and $R^7$ is sodium (identified in the art as octimibate sodium) has been described as possessing anti-aggregator activity and is under clinical development as an antihyperlipidemic agent.

SUMMARY OF THE INVENTION

In its broadest aspect, this invention is concerned with oxazole derivatives having Formula I and Formula II

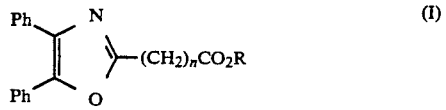

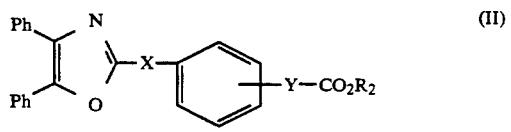

wherein R, $R_1$, $R_2$, X, Y, and n are defined below which are inhibitors of adenosine diphosphate and collagen-induced aggregation of human platelet-rich plasma and are particularly useful as inhibitors of mammalian blood platelet aggregation.

Another embodiment of the invention relates to the alkali metal salts of carboxylic acids of Formula I (R is hydrogen) and Formula II ($R_2$ is hydrogen). A further embodiment concerns pharmaceutical compositions comprised of a Formula I or II compound combined with at least one pharmaceutically acceptable excipient. Yet another embodiment relates to a method for inhibiting blood platelet aggregation in a mammal which comprises administering a therapeutically effective amount of a compound of Formula I or an alkali metal salt thereof where R is hydrogen or a Formula II compound or an alkali metal salt thereof where $R_2$ is hydrogen to a mammal in need of such treatment.

DETAILED DESCRIPTION OF THE INVENTION

This invention relates to inhibitors of mammalian blood platelet aggregation OF Formula I

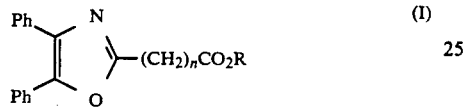

wherein n is 7-9 and R is hydrogen or lower alkyl; or when R is hydrogen, the alkali metal salt thereof.

The compounds of the instant invention are further characterized by Formula II

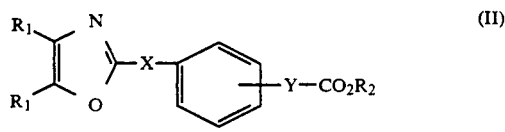

wherein
- $R_1$ is phenyl or thienyl;
- $R_2$ is hydrogen, lower alkyl or together with $CO_2$ is tetrazol-1-yl;
- X is a divalent connecting group selected from the group consisting of $CH_2CH_2$, $CH=CH$, and $CH_2O$;
- Y is a divalent connecting group attached to the 3-or 4-phenyl position selected from the group consisting of $OCH_2$, $CH_2CH_2$ and $CH=CH$, or when $R_2$ is hydrogen, an alkali metal salt thereof.

It is understood that as used herein limitations of Formula I and II are defined as follows.

The term "lower alkyl" refers to a branched or unbranched saturated hydrocarbon chain containing from 1-4 carbon atoms; specifically, methyl, ethyl, n-propyl, isopropyl, n-butyl, secondary butyl, and tertiary butyl.

The term "lower alkanol" denotes an alcohol having 1-4 carbon atoms defined by "lower alkyl".

The symbol "Ph" represents phenyl.

The term "alkali metal salts" comprehends the alkali metals and most preferably sodium and potassium.

When the "divalent connecting group X is $CH_2O$", carbon is covalently bonded to the oxazole and oxygen is covalently bonded to the substituted phenyl grouping.

When the "divalent connecting group Y is $OCH_2$", oxygen is covalently bonded to phenyl and carbon is covalently bonded to the carboxylic function.

According to the present invention, the compounds characterized by Formula 1, as defined above, are obtained by a process comprising:

(a) hydrolyzing a compound of Formula $I^a$

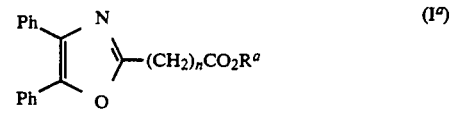

wherein n is 7-9 and $R^a$ is lower alkyl to the corresponding acid, or (b) esterifying a compound of Formula $I^b$

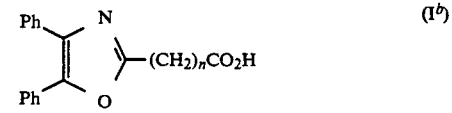

wherein n is 7-9 with a lower alkanol, or (c) reacting a keto ester of Formula III

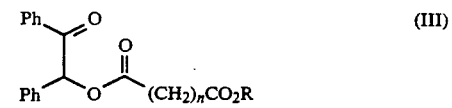

wherein n is 7-9 and R is hydrogen or lower alkyl with ammonium acetate to form the corresponding oxazole, or (d) decarboxylating a substituted malonic acid of Formula IV

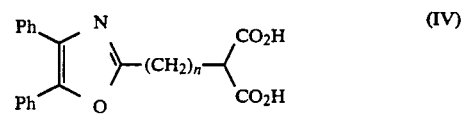

wherein n is 6-8.

Scheme 1 below illustrates the foregoing process.

Scheme 1

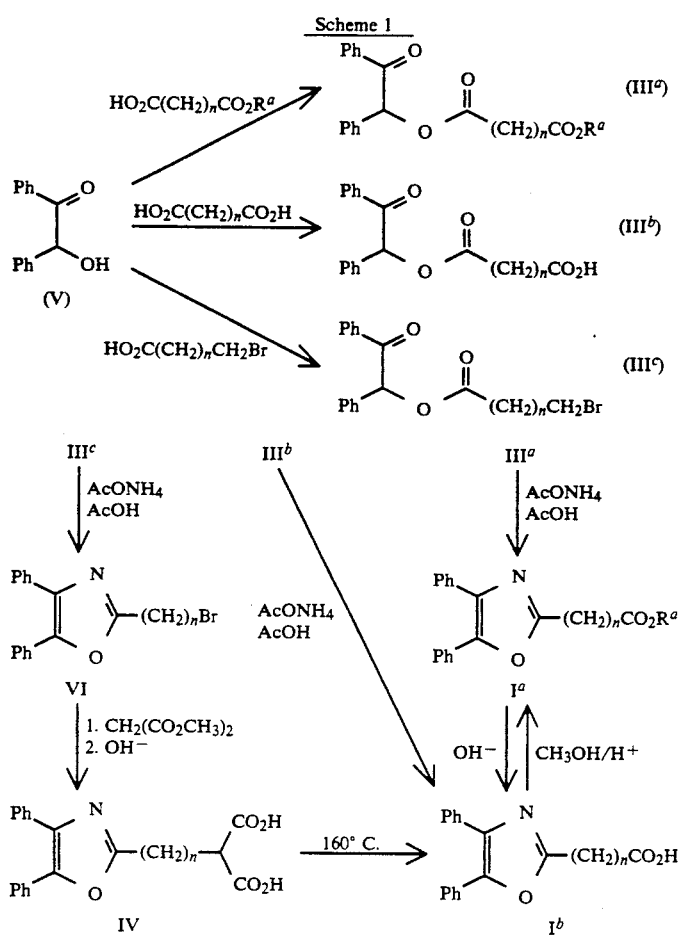

In general, oxazole ring formation is conventionally accomplished by treating a keto ester with an excess of ammonium acetate in acetic acid at reflux temperature. The keto esters (III$^{a,b,c}$) are obtained by esterifying benzoin with an appropriately substituted carboxylic acid. For example, keto ester (III$^a$) is obtained by coupling benzoin (V) and the half ester of the dicarboxylic acid HO$_2$C(CH$_2$)$_n$CO$_2$R$^a$ where n is 7-9 and R$^a$ is lower alkyl using 1,3-dicyclohexylcarbodiimide in the presence in a catalytic amount of 4-dimethylaminopyridine according to the procedure of H. H. Wasserman, et al., Tetrahedron, 37, 4059-4064 (1981). Purification is not required and the keto ester (III$^a$) treated with an excess of ammonium acetate in acetic acid at reflux temperature provides oxazole (I$^a$). Hydrolysis of the ester functionality with aquous hydroxide provides the corresponding acid (I$^b$).

Alternatively, oxazole (I$^b$) can be prepared by treating keto ester III$^c$, where n is 6-8, with ammonium acetate and acetic acid to provide the oxazole bromide intermediate (VI, n=6-8). Treating this intermediate with a 3-fold excess of dimethylmalonate and potassium t-butoxide in tetrahydrofuran (THF) at reflux in the presence of a catalytic quantity of 18-Crown ether-6 provides the methyl ester of (IV) which is saponified to diacid (IV) and thermally decarboxylated to give (I$^b$). Esterification of (I$^b$) is accomplished conventionally by heating the acid (I$^b$) in a lower alkanol in the presence of concentrated sulfuric acid.

Another approach to the preparation of (I$^b$) involves esterification of benzoin (V) with a three-fold excess of the dicarboxylic acid HO$_2$C(CH$_2$)$_n$CO$_2$H where n is 7-9 in the presence of a slight excess of 1,3-dicyclohexylcarbodiimide and a catalytic amount of 4-dimethylaminopyridine in methylene dichloride to provide the keto ester (III$^b$). Treatment of the crude keto ester (III$^b$) with ammonium acetate under standard conditions affords the oxazole acid (I$^b$) which is separated from by-products by column chromatography.

Alkali metal salts of Formula I carboxylic acids are conventionally prepared by dissolving the acid in methanol with a molar equivalent of an alkali base such as sodium methoxide and precipitating the salt or removing the solvent.

According to the present invention, the compounds characterized by Formula II

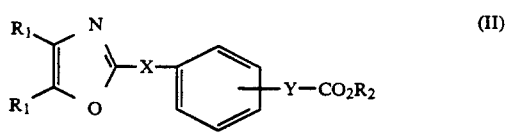

wherein

R$_1$ is phenyl or thienyl;

R$_2$ is hydrogen, lower alkyl or together with CO$_2$ is tetrazol-1-yl;

X is a divalent connecting group selected from the group consisting of CH$_2$CH$_2$, CH=CH and CH$_2$O; and Y is a divalent connecting group selected from the group consisting of OCH$_2$, CH$_2$CH$_2$ and CH=CH are obtained by a process comprising:

(a) hydrolyzing a compound of Formula II$^a$

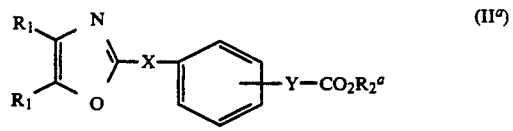

wherein R$_2{}^a$ is lower alkyl and R$_1$, X and Y are as defined above to the corresponding acid; or (b) esterifying a compound of Formula (II$^b$)

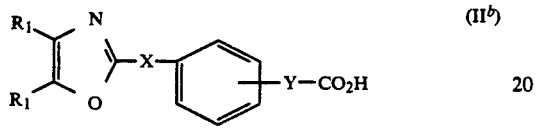

wherein R$_1$, X and Y are as defined above with a lower alkanol; or (c) reducing a compound of Formula (III)

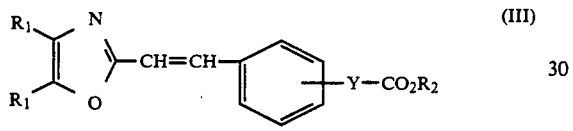

wherein R$_1$, R$_2$ and Y are as defined above to provide a compound of Formula (IV)

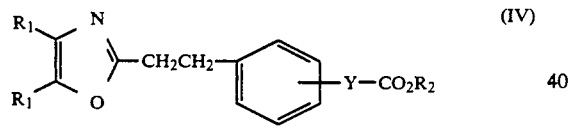

wherein R$_1$, R$_2$ and Y are as defined above, (d) alkylating a compound of Formula (V)

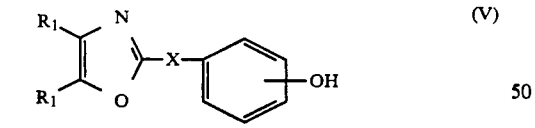

wherein R$_1$ and X are as defined above and OH is attached to the 3 or 4 phenyl position with BrCH$_2$CO$_2$R$_2{}^a$ wherein R$_2{}^a$ is lower alkyl to provide a compound of Formula (VI)

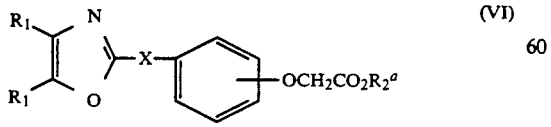

wherein R$_2{}^a$ is lower alkyl, R$_1$ is as defined above, and X is CH$_2$H$_2$, CH=CH; or (e) alkylating a 3 or 4 substituted phenyl of Formula (VII)

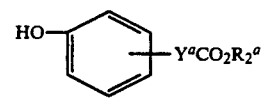

wherein Y$^a$ is CH$_2$O or CH$_2$CH$_2$ and R$_2{}^a$ is lower alkyl with an oxazole of Formula (VIII)

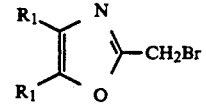

wherein R$_1$ is phenyl or thienyl to provide a compound of Formula (IX)

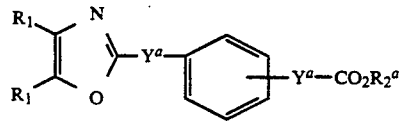

wherein R$_1$ and R$_2$' are as defined above and Y$^a$ is CH$_2$O or CH$_2$CH$_2$, (f) reacting the trifluoromethanesulfonate ester of a compound of Formula (X)

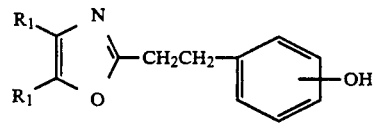

wherein R$_1$ is phenyl or thienyl and OH is attached to the 3 or 4 phenyl position with H$_2$C=CHCO$_2$R$_2{}^a$ wherein R$_2{}^a$ is lower alkyl to provide a compound of Formula (XI)

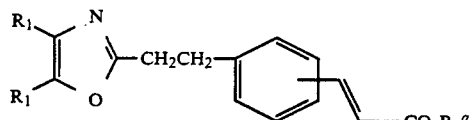

wherein R$_1$ is phenyl or thienyl and R$_2{}^a$ is lower alkyl, (g) reacting a compound of Formula (XII)

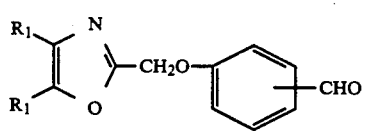

wherein R$_1$ is phenyl and the formyl grouping is attached to the 3 or 4 phenyl position with the trimethylphosphonate derivative of CH$_2$CO$_2$R$_2{}^a$ wherein R$_2{}^a$ is lower alkyl to provide a compound of Formula (XIII)

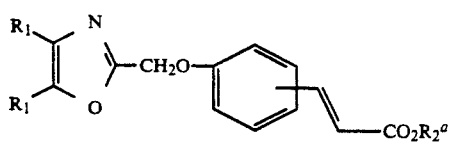

(XIII)

wherein $R_1$ and $R_2^a$ are as defined above,
(h) reacting a compound of Formula (XIV)

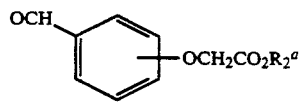

(XIV)

wherein $R_2^a$ is lower alkyl and the side chain is attached to the 3 or 4 phenyl position with a phosphonate oxazole of Formula (XV)

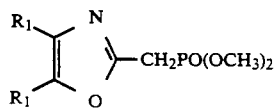

(XV)

wherein $R_1$ is phenyl or thienyl to provide a compound of Formula (XVI)

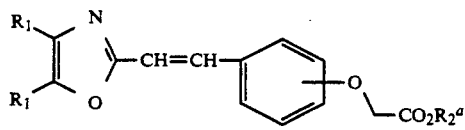

(XVI)

wherein $R_1$ is phenyl or thienyl and $R_2^a$ is lower alkyl,
(i) treating a compound of Formula (XVII)

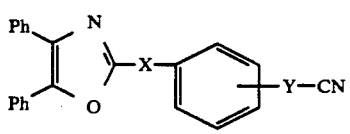

(XVII)

wherein X and Y are as defined above with tri-n-butyltin azide to provide a tetrazole of Formula (XVIII)

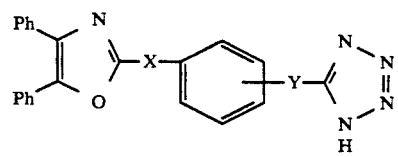

(XVIII)

wherein X and Y are as defined above.

The following schemes for preparation of representative compounds of Formula II illustrate the foregoing process.

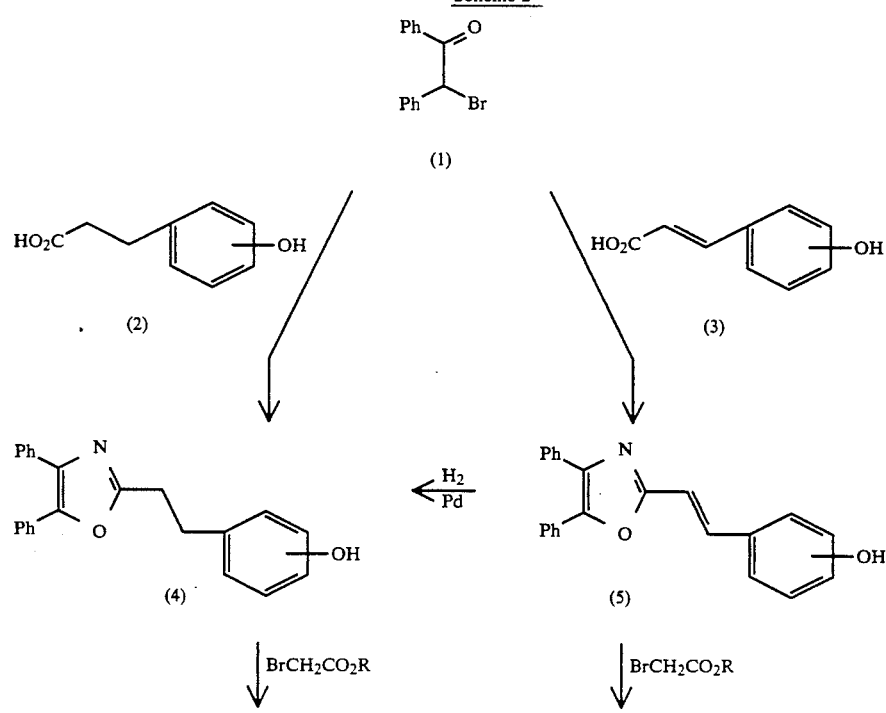

-continued
Scheme 2
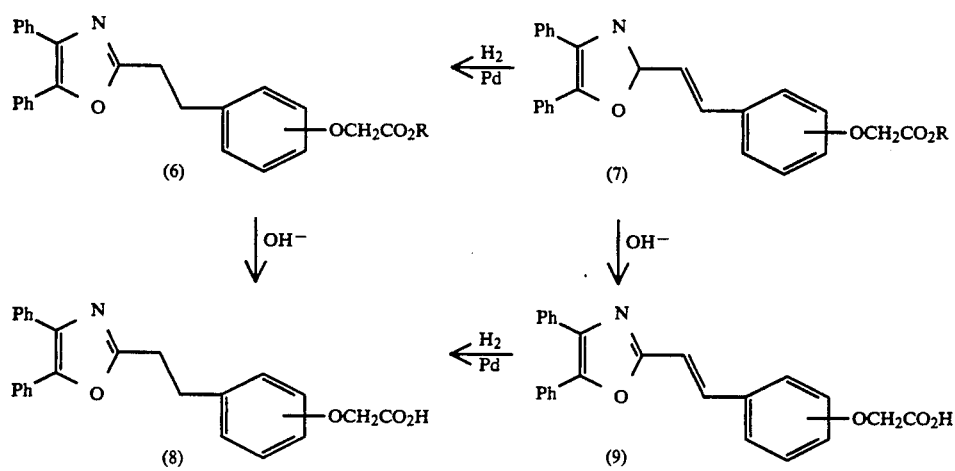
Scheme 3
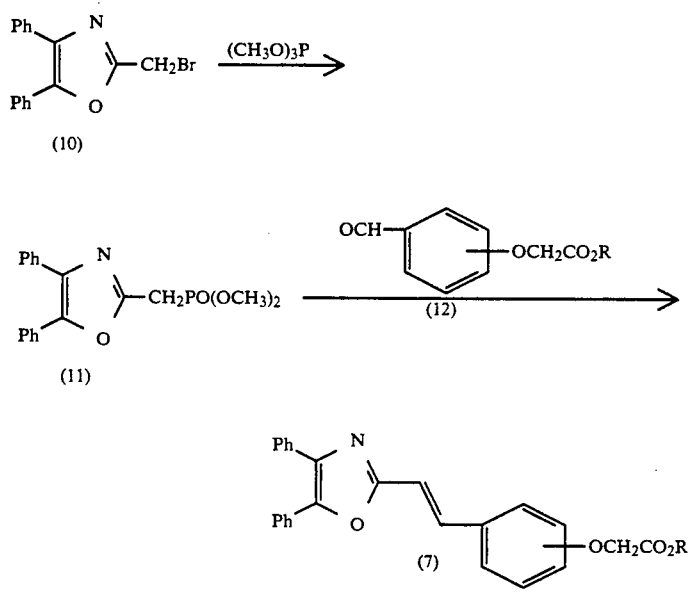
Scheme 4
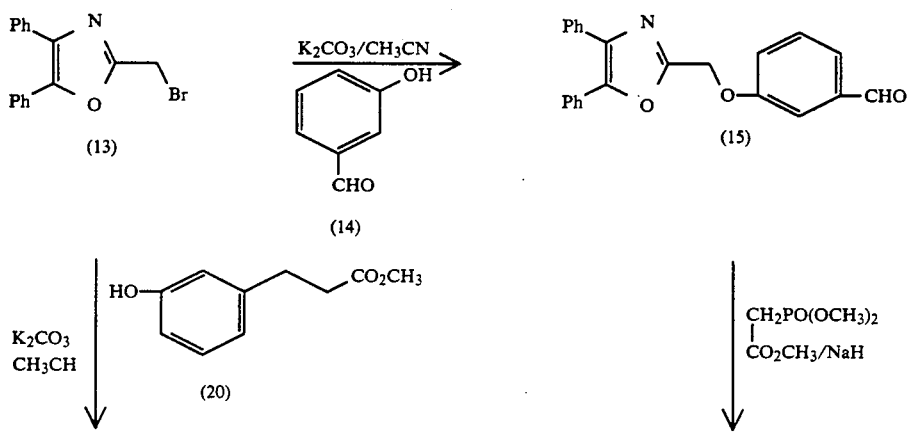

5,262,540
-continued
Scheme 4
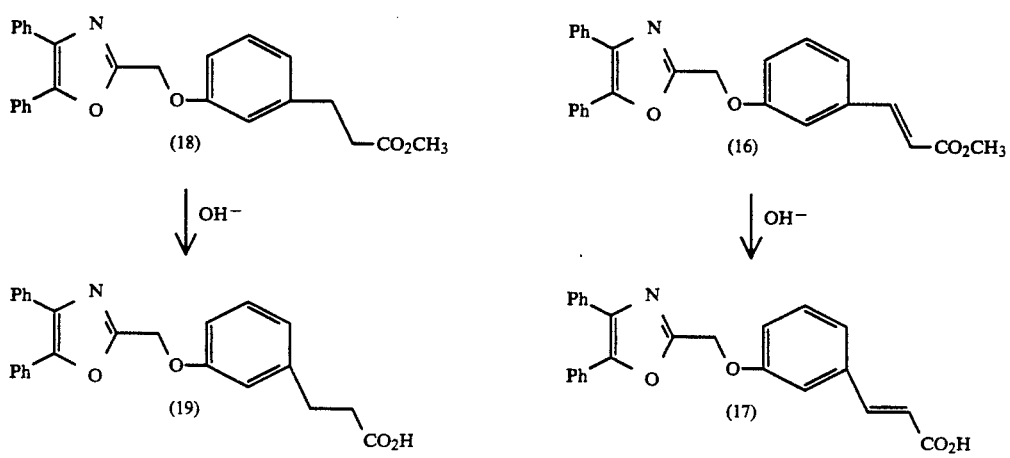
Scheme 5
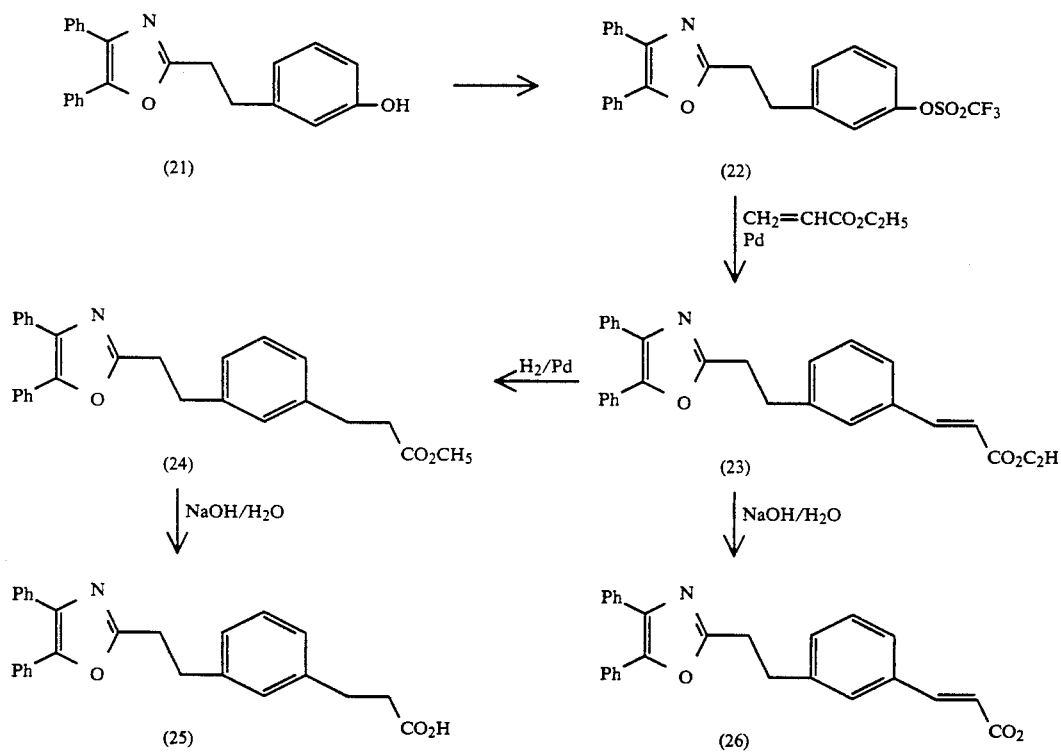
Scheme 6
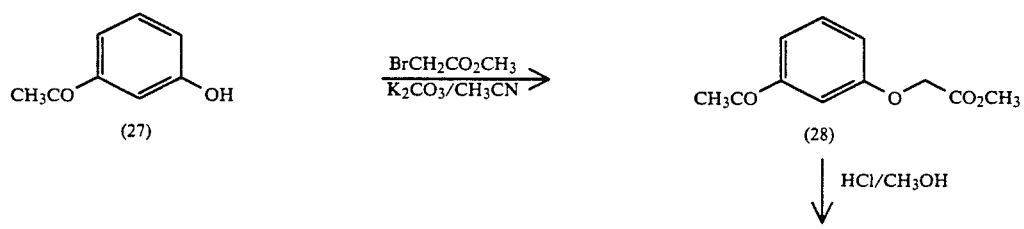

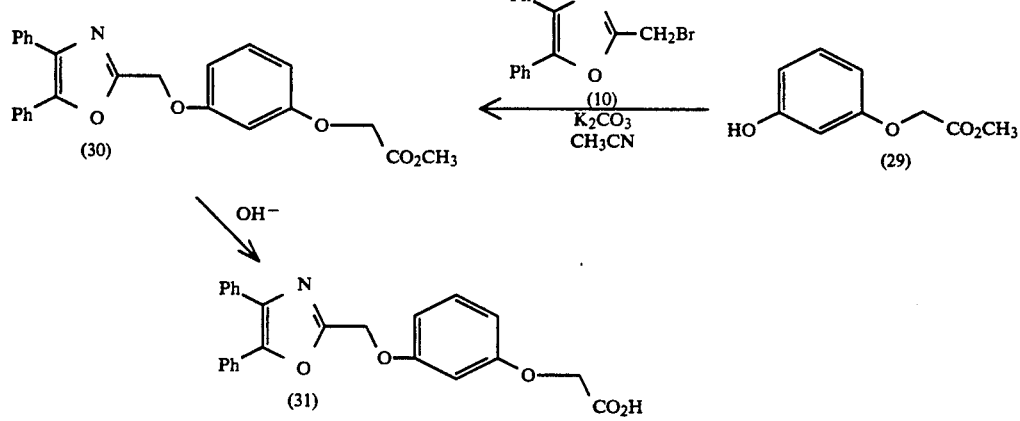

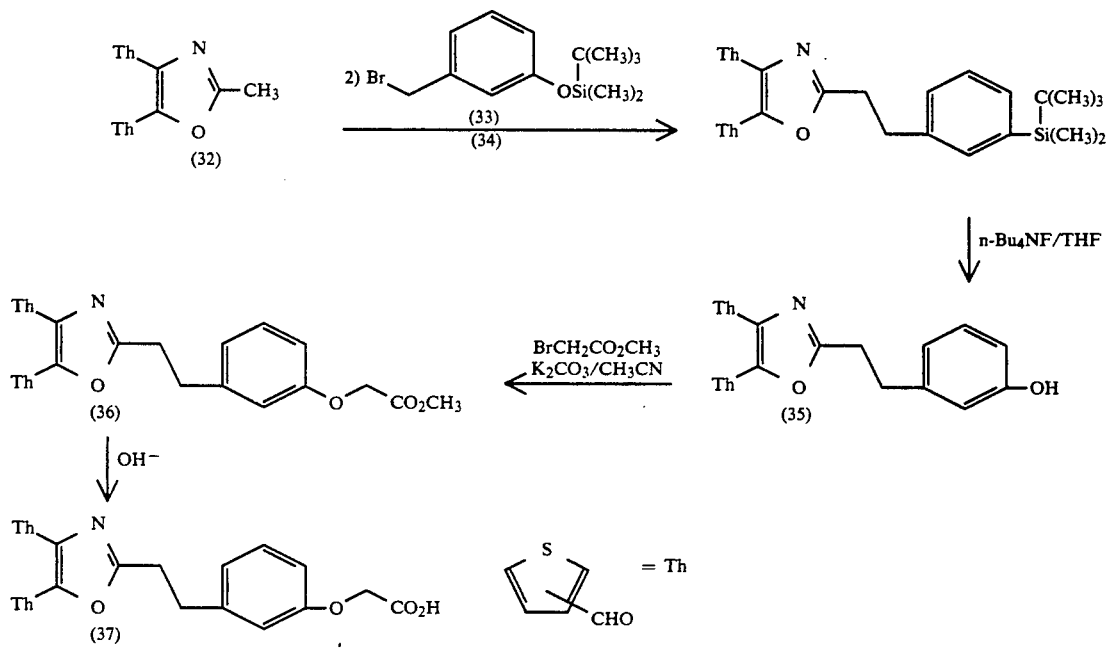

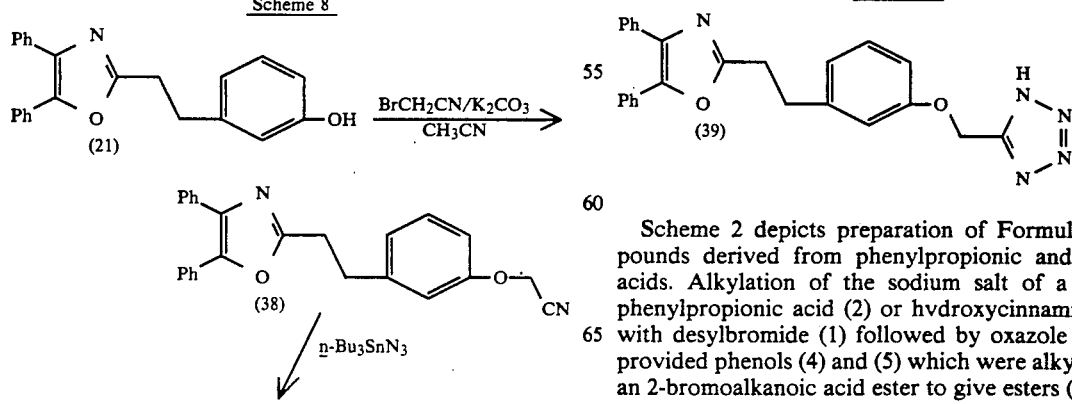

Scheme 2 depicts preparation of Formula II compounds derived from phenylpropionic and cinnamic acids. Alkylation of the sodium salt of a hirdroxyphenylpropionic acid (2) or hvdroxycinnamic acid (3) with desylbromide (1) followed by oxazole formation provided phenols (4) and (5) which were alkylated with an 2-bromoalkanoic acid ester to give esters (6) and (7), respectively. Subsequent hydrolysis with aqueous alkali provided the corresponding acids (8) and (9). The saturated compounds (6) and (8) were synthesized from the unsaturated precursors (7) and (9) by way of hydrogenation, preferably catalytic, which also could be carried out at the phenolic stage as shown.

Scheme 3 depicts an alternate approach to the preparation of esters (7) involving coupling of the dimethylphosphonate (11) prepared from bromide (10) via an Arbuzov reaction described by D.C. Schroeder, et al., *J. Org. Chem.*, 27, 1098-1101 (1962) with a functionalized aldehyde (12). Proton NMR data indicated that the unsaturated compounds were predominantly, if not exclusively, of the trans configuration.

Scheme 4 depicts preparation of Formula II compounds incorporating an oxygen atom in the linkage between the aryl and oxazole rings. Bromination of 4,5-diphenyl-2-methyloxazole according to a modification of the procedure of D.L. Aldous, et al., *J. Org. Chem.*, 25, 1151-1154 (1960) using N-bromosuccinimide in carbontetrachloride at reflux in the presence of 2,2'-azobis(2-methylpropionitrile) provided bromide (13). Alkylating the hydroxy benzaldehyde (14) with bromide (13) in the presence of potassium carbonate in refluxing acetonitrile produced aldehyde (15) which was converted to ester (16) by way of the Wadsworth-Emmons modification of the Wittig reaction according to W.S. Wadsworth, *Org. Reactions*, 25, 73-253 (1978). Conventional alkaline hydrolysis of ester (16) gave carboxylic acid (17). Saturated ester (18) and acid (19) were sinthesized by alkylating the ester of 3-hydroxyphenylpropionic acid (20) in the presence of potassium carbonate and subsequent hydrolysis.

Scheme 5 depicts the preparation of compounds of Formula II wherein the connecting radical Y is "$CH_2CH_2$" to and X is $CH_2CH_2$ or $CH=CH$. The triflate (22) was synthesized from the oxazole phenol (21) by treatment with trifluoromethanesulfonic anhydride in pyridine. Reacting the trifluoromethanesulfonate ester (22) with ethyl acrylate in the presence of a Pd catalyst afforded cinnamic ester (23). Base-induced hydrolysis of (23) gave acid (26). Catalytic hydrogenation of the cinnamic ester (14) provided saturated ester (24) which was converted to acid (25) under aqueous alkaline conditions.

Scheme 6 illustrates the preparation of compounds of Formula II when the "X connecting group" is $CH_2O$ and the "Y-side chain connecting group" is $OCH_2$. Resorcinol monoacetate (27) was alkylated with methyl bromoacetate to give (28) which was dissolved in methanolic hydrogen chloride solution to provide phenol (29). Alkalation of phenol (29) with bromide (10) provided the oxazole ester (30) which was hydrolyzed to carboxylic acid (31) using aqueous hydroxide solution.

Scheme 7 illustrates the preparation of compounds of Formula II wherein the two phenyl rings are replaced by thiophene rings in the two possible regio-isomeric forms. The 2-methyl-4,5-(2- or 3-thienyl) oxazole derivatives (32) were obtained by the method of D. Davidson, et al., *J. Org. Chem.*, 2, 328-334 (1937) from 2- or 3-thiophene carboxaldehyde. Metalation of (32) using n-butyllithium followed by benzyl bromide (33) provided oxazoles (34). The phenolic protecting group dimethyl(1,1-dimethylethyl)silane was removed using n-butylammonium fluoride to furnish phenols (35). Conventional alkylation with methyl bromoacetate gave esters (36) which were hydrolyzed to carboxylic acids (37) with aqueous hydroxide solution.

Scheme 8 illustrates preparation of compounds of Formula II wherein the carboxylic acid moiety is replaced with the tetrazole heterocycle. Treatment of phenol (21) with bromoacetonitrile and potassium carbonate gave nitrile (38) which was converted to the tetrazole (39) with tri-n-butyltin azide.

Alkali metal salts of Formula II carboxylic acis are conventionally prepared by dissolving the acid in a suitable solvent such as methanol, adding a molar equivalent of an alkali base such as sodium methoxide, and precipitating the salt or removing the solvent.

As stated above, the compounds of Formula I and Formula II have pharmacological properties which make them particularly useful as inhibitors of blood platelet aggregation.

Platelet aggregation is considered part of a complex physiological mechanism for formation of a thrombus in the vascular system. Thromboembolic phenomena, i.e., the formation of thrombi, are involved in hemostasis and a number of diseased states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few and in ischaemic heart disease, artherosclerosis, multiple sclerosis, intracranial tumors, thromboembolism, and hyperlipemia; refer to A. Poplawski, et al., *J. Artherosclerosis Research*, 8, 721 (1968). Thus, the compounds of the invention which have antithrombogenic (inhibit blood platelet aggregation) are useful in prevention or treatment of conditions involving platelet aggregation and thrombosis such as the above. The instant compounds are also considered to have antimetastatic potential in view of their platelet inhibition properties.

The pharmacological properties of the instant compounds can be demonstrated by conventional in vitro and in vivo biological tests such as the following.

IN VITRO INHIBITION OF HUMAN PLATELET AGGREGATION

The aggregometer method of Born, C.V.R., *J. Physiol.*, (London), 1962, 162, 67-68, as modified by Mustard, J.F., et al., *J. Lab. Clin. Med.* 1964, 64, 548-599 was used to assess the in vitro activity of the various compounds as to the inhibition of adenosine diphosphate (ADP) and collagen-induced platelet aggregation. The human volunteer donor's arm is cleansed with 70% ethyl alcohol. A sterile 20 ml syringe and needle are used to withdraw 20 ml of blood. The blood is immediately added to a test tube containing 3.8% sodium citrate to prevent clotting (1 part citrate to 9 parts blood).

Platelet rich plasma (PRP) was separated by centrifugation for 10 minutes at 1000 rpm (140×g) from citrated (3.8%) human blood. All glassware used for preparation of PRP is silicon treated. ADP in final concentration of 0.5 mcg/ml or 0.05 mL of a collagen suspension prepared according to the method described by Evans, G., et al., *J. Exp. Med.*, 1968, 128, 877-894 was used to induce aggregation. The various compounds tested were dissolved in dimethylsulfoxide (DMSO) so that 5 mcl added to the platelet rich plasma would yield the desired test concentration. Vehicle control trials were done and compared with aggregation induced in platelet rich plasma containing various concentrations of the test compounds. Dose response curves were obtained and Inhibitor Concentration (IC$_{50}$) values calculated or the percent inhibition at 32 mcg/ml noted. In this test, the IC$_{50}$ values for dipyridamole, a clinically useful antithrombogenic agent, are 512 mcg/ml vs. ADP and 245 mcg/ml vs collagen. Results are given in Tables I, II and III hereinafter for various Formula I and II compounds and related prior art compounds.

TABLE I

Inhibition of Human Platelet Aggregation of Formula I Compounds

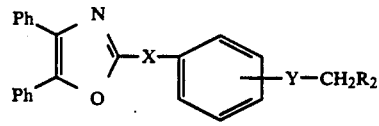

| Example | n | R | vs ADP mcg/ml | % | vs. Collagen mcg/ml | % |
|---|---|---|---|---|---|---|
| 1 | 8 | CH$_3$ | 32 | 2 | 32 | 83 |
| 2 | 8 | H | 2.5 | 50 | 1.4 | 50 |
| 3 | 7 | CH$_3$ | 32 | 0 | | |
| 4 | 7 | H | 32 | 4 | 11 | 50 |
| (a)* | 2 | H | 32 | 16 | 32 | 36 |
| (a) | 3 | H | 32 | 0 | | |
| (a) | 1 | H | 32 | 0 | | |

(a) U.S. Pat. No. 3,578,671
*Oxaprozin

It is evident that the acids of Formula I (Examples 2 and 4) are active whereas the short chain acids of U.S. Pat. No. 3,578,671 are essentially inactive against ADP-/collagen-induced aggregation of human platelets. As for the esters (Examples 1 and 3) corresponding to Examples 2 and 4, they are relatively weak anti-aggregators in vitro but serve as pro drugs in vivo where they are readily hydrolyzed to the active acids.

TABLE II

Inhibition of Human Platelet Aggregation of Formula II Compounds Wherein R$_1$ is Phenyl

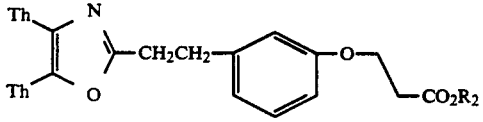

| Ex. | Ring Position | X | Y | R$_2$ | vs ADP mcg/mL (%) | vs. Collagen mcg/mL (%) |
|---|---|---|---|---|---|---|
| 5 | 3 | CH$_2$CH$_2$ | OCH$_2$ | CH$_3$ | 0.29 (50) | 0.25 (50) |
| 6 | 3 | CH$_2$CH$_2$ | OCH$_2$ | H | 0.49 (50) | 0.12 (50) |
| 7 | 4 | CH$_2$CH$_2$ | OCH$_2$ | CH$_3$ | 7.4 (50) | 2.9 (50) |
| 8 | 4 | CH$_2$CH$_2$ | OCH$_2$ | H | 3.7 (50) | 1.6 (50) |
| 9 | 3 | CH$_2$CH$_2$ | CH=CH | C$_2$H$_5$ | 32 (26) | |
| 10 | 3 | CH$_2$CH$_2$ | CH=CH | H | 0.3 (50) | |
| 11 | 3 | CH$_2$CH$_2$ | CH$_2$CH$_2$ | C$_2$H$_5$ | 32 (35) | |
| 12 | 3 | CH$_2$CH$_2$ | CH$_2$CH$_2$ | H | 6.5 (50) | |
| 13 | 3 | CH=CH | OCH$_2$ | CH$_3$ | 3.1 (50) | 0.2 (50) |
| 14 | 3 | CH=CH | OCH$_2$ | H | 5.3 (50) | 0.39 (50) |
| 15 | 4 | CH=CH | OCH$_2$ | CH$_3$ | 15 | |
| 16 | 4 | CH=CH | OCH$_2$ | H | 4.05 | |
| 21 | 3 | CH$_2$O | CH=CH | CH$_3$ | 32 (3) | 32 (6) |
| 22 | 3 | CH$_2$O | CH=CH | H | 5.5 (50) | 1.8 (50) |
| 23 | 4 | CH$_2$O | CH=CH | CH$_3$ | 32 (19) | 32 (71) |
| 24 | 4 | CH$_2$O | CH=CH | H | 32 (24) | 32 (73) |
| 17 | 3 | CH$_2$O | CH$_2$CH$_2$ | CH$_3$ | 32 (0) | 32 (47) |
| 18 | 3 | CH$_2$O | CH$_2$CH$_2$ | H | 32 (24) | 32 (89) |
| 19 | 4 | CH$_2$O | CH$_2$CH$_2$ | CH$_3$ | 32 (29) | 24 (50) |
| 20 | 4 | CH$_2$O | CH$_2$CH$_2$ | H | 20 (50) | 5 (50) |
| 25 | 3 | CH$_2$O | OCH$_2$ | CH$_3$ | 1.9 (50) | |

TABLE II-continued

Inhibition of Human Platelet Aggregation of Formula II Compounds Wherein R$_1$ is Phenyl

| Ex. | Ring Position | X | Y | R$_2$ | vs ADP mcg/mL (%) | vs. Collagen mcg/mL (%) |
|---|---|---|---|---|---|---|
| 26 | 3 | CH$_2$O | OCH$_2$ | H | 0.27 (50) | |

TABLE III

Inhibition of Human Platelet Aggregation of Thienylated Oxazoles

| Example | Th | R$_2$ | vs. ADP mcg/mL | % |
|---|---|---|---|---|
| 29 | S (thienyl) | CH$_3$ | 3.9 | 50 |
| 30 | S (thienyl) | H | 7.1 | 50 |
| 32 | S (thienyl) | H | 3.1 | 50 |

IN VIVO INHIBITION OF BIOLASER INDUCED THROMBOSIS

The laser induced thrombosis method is a modification of the technique developed by Sanders, A.G., et al. in *Brit. J. Exp. Pathol.*, 1954, 35, 331 and Grant, L., et al. in *Proc. Soc. Exp. Biol. Med.*, 1965, 119, 1123. A detailed description of this method has been described by Fleming, J.S., et al. in *Platelets and Thrombosis*, A. Scriabine and S. Sherry, eds., Baltimore, Univ. Park Press, pp. 247–262, 1974 and is hereby incorporated by reference.

Briefly, Lucite ear chambers were chronically implanted in adult, English lop-ear rabbits. The animals were conditioned to lie quietly in the supine position. Localized microvascular injury was induced by focusing a single ruby laser beam through a microscope into the lumen of a vessel 10–60 mcM in diameter. This evoked the formation of a small thrombus consisting of platelets accumulated around a core of one or two damaged red cells. Thrombus area was determined as a product of two perpendicular measurements made by using a micrometer eye piece. The mean thrombus area (mcM$^2$) obtained for 10 trials in each rabbit served as a control value. The test compound was administered orally and post-dose trials were performed at selected times. Pharmacological activity was evaluated by comparing pre- and post-dose mean thrombus areas.

In the above biolaser model of thrombosis, the compound of Example 6 exhibited 53% inhibition of thrombosis at an oral dose of 10 mg/kg, 38% inhibition at 3 mg/kg and 23% inhibition at 1 mg/kg body weight.

The dosage employed in the therapeutic methods of the instant invention will vary with the form of administration, the particular compound chosen, the subject being tested and the effect desired. Suitable effective doses in animals range from 0.1-50 mg/kg body weight orally and from 0.05-10 mg/kg body weight parenterally (generally characterized as subcutaneous, intramuscular, and intravenous injection). It is contemplated that the effective unit dose in man will range from 1 to 100 mg and preferably from 0.5 to 20 mg administered one to three times a day. In accordance with conventional clinical practice, the effective dose can be determinted by administering a Formula I or II compound at a dosage substantially less than the dose of the compound which is thought to be effective and then increasing the dosage in small increments until the desired effect is achieved.

In carrying out the instant therapeutic methods, the active ingredient of Formula I or II or alkali metal salts of Formula I and II carboxylic acids are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspension, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including indert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspension, syrups and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectible compositions are formulted as known in the art and may contain appropriate dispersing or wetting agents and suspending agents identical or similar to those mentioned above.

The following examples are given by way of illustration and are not to be construed as limiting the invention in any way inasmuch as many variations of the invention are possible within the spirit of the invention.

DESCRIPTION OF SPECIFIC EMBODIMENTS

In the following examples, all temperatures are given in degrees Centigrade. Melting points were recorded on a Thomas-Hoover capillary melting point apparatus and are uncorrected. Proton magnetic resonance ($^1$H-NMR) spectra were recorded on a Bruker AM 300, Bruker WM 360 or Varian Gemini spectrometer. All spectra were determined in $CDCl_3$ or $DMSO$-$d_6$ unless otherwise indicated and chemical shifts are reported in delta units downfield from the internal standard tetramethylsilane (TMS) and interproton coupling constants are reported in Hertz (Hz). Splitting patterns are designated as follows: s, singlet; d, doublet; t, triplet; q, quart; m, multiplet; br, broad peak; and dd, doublet of doublet.

EXAMPLE 1

Methyl 4,5-diphenyl-2-oxazolenonanoate

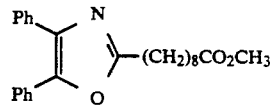

A mixture of 4,5-diphenyl-2-oxazole nonanoic acid (800 mg, 2 mmol), methanol (2 mL) and concentrated sulfuric acid (2 drops) was heated to reflux. After 2 hours, the solvent was evaporated and the residue partitioned between $CH_2Cl_2$ and water. The organic phase was separated, washed with saturated $NaHCO_3$ solution, dried over sodium sulfate and concentrated in vacuo to leave an oil. Chromatography on a column of silica gel using a mixture of hexanes and diethyl ether (4:1) as eluent gave methyl 4,5-diphenyl-2-oxazolenonanoate (800 mg, 96%).

Anal. Calcd. for $C_{25}H_{29}NO_3$: C, 76.70; H, 7.47; N, 3.58. Found: C, 76.61; H, 7.84; N, 3.94%.

$^1$H-NMR ($CDCl_3$) delta: 1.20 to 1.50 (8H, m), 1.64 (2H, quintet, J=7 Hz), 1.87 (2H, quintet, J=7 Hz), 2.32 (2H, t, J=7.5 Hz), 2.87 (2H, t, J=7.5 Hz), 3.67 (3H, s), 7.20 to 7.50 (6H, m) and 7.60 to 7.80 (4H, m).

EXAMPLE 2

4,5-Diphenyl-2-oxazolenonanoic Acid

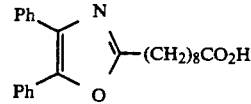

2-[7-(4,5-Diphenyl-1-oxazolyl)heptyl]propanedioic acid (4.50 g, 10 mmol) was heated with stirring at 150° C. After 2 hours, the flask was cooled and the residue triturated with a mixture of hexane and diethyl ether (1:1) to give a white solid. Crystallization from aqueous isopropyl alcohol afforded 4,5-diphenyl-2-oxazolenonanoic acid (3.15 g, 87%) m.p. 83°-85° C.

Anal. Calcd. for $C_{24}H_{27}NO_3$: C, 76.37; H, 7.22; N, 3.72. Found: C, 76.37; H, 7.21; N, 3.66%.

$^1$H-NMR ($DMSO$-$d^6$) delta: 1.10 to 1.40 (8H, m), 1.46 (2H, m), 1.71 (2H, m), 2.15 (2H, t, J=7 Hz), 2.76 (2H, t, J=7 Hz), 7.20 to 7.45 (6H, m), 7.45 to 7.65 (4H, m) and 11.99 (1H, bs).

EXAMPLE 3

Methyl 4,5-diphenyl-2-oxazoleoctanoate

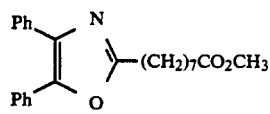

A mixture of benzoin (6.00 g, 28 mmol), azelaic acid monomethyl ester (7.17 g of 92% pure material, 32 mmol), 1,3-dicyclohexylcarbodiimide (7.00 g, 34 mmol), 4-dimethylaminopyridine (catalytic amount) and dichloromethane (120 mL) was stirred at room temperature. After 16 hours, the mixture was filtered and the solvent evaporated. Ammonium acetate (10.90 g, 141 mmol) and acetic acid (150 mL) were added to the residue and the mixture heated at reflux for 65 minutes before being cooled and diluted with water. The mixture was extracted with diethyl ether, the combined extracts dried over sodium sulfate and concentrated in vacuo. The residual oil was chromatographed on a column of silica gel using a mixture of hexanes and diethyl ether (7:3) as eluent to give methyl 4,5-diphenyl-2-oxazoleoctanoate (8.24 g, 77%) as an oil.

Anal. Calcd. for $C_{24}H_{27}NO_3$: C, 76.37; H, 7.22; N, 3.72. Found: C, 76.25; H, 7.28; N, 4.05%.

$^1$H-NMR (CDCl$_3$) delta: 1.10 to 1.35 (6H, m), 1.45 (2H, quintet, J=7 Hz), 1.67 (2H, quintet, J=7 Hz), 2.12 (2H, t, J=7.5 Hz), 2.66 (2H, t, J=7.5 Hz), 3.47 (3H, s), 7.05 to 7.25 (6H, m), and 7.35 to 7.55 (4H, m).

EXAMPLE 4

4,5-Diphenyl-2-oxazoleoctanoic Acid

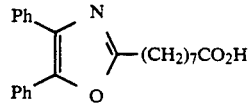

A mixture of methyl 4,5-diphenyl-2-oxazoleoctanoate (7.00 g, 18.5 mmol), 5N sodium hydroxide solution (7.42 mL), water (100 mL) and methanol (20 mL) was heated on a steam bath for 45 minutes. After stirring at room temperature for 75 minutes, the mixture was diluted with water (150 mL), heated on a steam bath for 10 minutes and then allowed to stir overnight at room temperature. The mixture was heated to reflux for 1 hour, cooled, acidified with 2N hydrochloric acid solution and extracted with CH$_2$Cl$_2$. The combined extracts were dried over sodium sulfate and concentrated in vacuo to give an oil that crystallized. Recrystallization from a mixture of diethyl ether, CH$_2$Cl$_2$ and hexanes furnished 4,5-diphenyl-2-ozazoleoctanoic acid (5.25 g, 77%), m.p. 70°-73° C.

Anal. Calcd. for $C_{23}H_{25}NO_3$: C, 76.01; H, 6.94; N, 3.86. Found: C, 75.87; H, 6.94; N, 4.16%.

$^1$H-NMR (CDCl$_3$) delta: 1.20 to 1.45 (6H, m), 1.54 (2H, quintet, J=7 Hz), 1.75 (2H, quintet, J=7 Hz), 2.23 (2H, t, J=7.5 Hz), 2.76 (2H, t, J=7.5 Hz), 7.10 to 7.35 (6H, m), 7.40 to 7.60 (4H, m) and 11.74 (1H, bs).

EXAMPLE 5

Methyl 2-[3-[2-(4,5-diphenyl-2-oxazolyl)ethyl]phenoxy]acetate

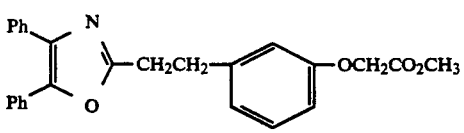

A mixture of 3-[49-(4,5-diphenyl-2-oxazolyl)ethyl]phenol (3.41 g, 10 mmol), potassium carbonate (1.52 g, 11 mmol), potassium iodide (catalytic amount), methyl bromoacetate (1.68 g, 11 mmol) and acetonitrile (32 mL) was stirred at reflux under an atmosphere of nitrogen. After 90 minutes, the mixture was cooled, filtered and concentrated to leave an oil which was subjected to chromatography on a column of silica gel. Elution with a mixture of hexanes, ethyl acetate and triethylamine (75:25:1) afforded methyl 2-[3-[2-(4,5-diphenyl-2-oxazolyl)ethyl]phenoxy]acetate (3.59 g, 86%) as a viscous oil.

Anal. Calcd. for $C_{26}H_{23}NO_4$: 75.54; H, 5.61; N, 3.39. Found: C, 75.57; H, 5.67; N, 3.41%.

$^1$H-NMR (CDCl$_3$) delta: 3.14 (4H, s), 3.76 (3H, s), 4.60 (2H, s), 6.75 (1H, dd, J=8 Hz, J'=2.5 Hz), 6.90 (1H, d, J=8 Hz), 7.15 to 7.40 (7H, m) and 7.50 to 7.75 (4H, m).

EXAMPLE 6

2-[3-[2-(4,5-Diphenyl-2-oxazolyl)ethyl]phenoxy]acetic Acid

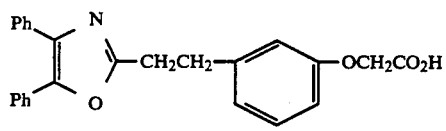

A mixture of methyl 2-[3-[2-(4,5-diphenyl-2-oxazolyl)ethyl]phenoxy]acetate (2.25 g, 5.5 mmol), 3N sodium hydroxide solution (5.5 mL) and methanol (50 mL) was heated to reflux on a steam bath. After 5 minutes, the mixture was cooled, the methanol evaporated and the residue diluted with water. Warming provided a solution which was diluted with 1N hydrochloric acid solution to pH 3 to give an oily precipitate. The mixture was extracted with CH$_2$Cl$_2$ and the organic extracts washed twice with water and once with saturated sodium chloride solution. Concentration, after drying over sodium sulfate, left a pale yellow solid which was recrystallized twice from a mixture of hexanes and CH$_2$Cl$_2$ (2:1) to give 2-[3-[2-(4,5-diphenyl-2-oxazolyl)-ethyl]phenoxy]acetic acid (1.74 g, 80%), m.p. 153.3°-154.5° C.

Anal. Calcd. for $C_{25}H_{21}NO_4$: C, 75.18; H, 5.30; N, 3.51. Found: C, 75.15; H, 5.35; N, 3.30%.

$^1$H-NMR (DMSO-d$^6$) delta: 3.12 (4H, m), 4.64 (2H, s), 6.73 (1H, dd, J=8 Hz, J'=2 Hz), 6.88 (2H, m), 7.20 (1H, t, J=8 Hz), 7.30 to 7.50 (6H, m), and 12.98 (1H, bs).

Sodium metal (0.58 g, 25 mg/atom) was dissolved in methanol (10 mL) and 1 mL, of this solution diluted with methanol (20 mL). 2-[3-[2-(4,5-Diphenyl-2-oxazolyl]ethyl]-phenoxy]acetic acid (100 g, 2.5 mmol) was added ant the mixture stirred at room temperature for 18 hours.

EXAMPLE 7

Methyl 2-[4-(2-(4,5-diphenyl-2-oxazolyl)ethyl]phenoxy]acetate

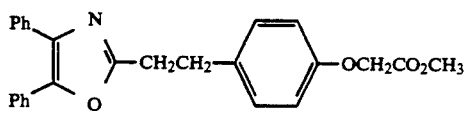

A mixture of 4-[2-(4,5-diphenyl-2-oxazolyl)ethyl]-phenol (6.00 g, 17 mmol), methyl bromoacetate (2.96 g, 1.83 mL, 19 mmol), potassium carbonate (2.91 g, 21 mmol), potassium iodide (catalyic amount) and acetonitrile (80 mL) was stirred at reflux. After 1 hour, the mixture was cooled, filtered and the solvent removed to leave a crystalline solid that was tritrated with hexanes and filtered to give methyl 2-[4-[2-(4,5-diphenyl-2-oxazolyl)ethyl]phenoxy]acetate (7.27 g, 100%). An analytical sample was obtained by recrystallizing a 2.25 g batch from methanol to give 1.70 g of pure material which had m.p. 122°-125° C.

Anal. Calcd. for $C_{26}H_{23}NO_4$: C, 75.53; H, 5.61; N, 3.39. Found: C, 75.30; H, 5.86; N, 3.39%.

$^1$H-NMR ($CDCl_3$) delta: 3.11 (4H, s), 3.77 (3H, s), 4.60 (2H, s), 6.84 (2H, d, J=8.5 Hz), 7.18 (2H, d, J=8.5 Hz), 7.20 to 7.50 (6H, m), and 7.60 to 7.80 (4H, m).

EXAMPLE 8

2-[4-[2-(4,5-Diphenyl-2-oxazolyl)-ethyl]phenoxy]acetic Acid

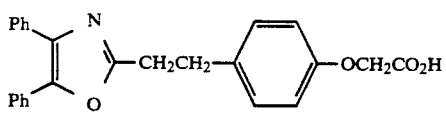

A mixture of methyl 2-[4-[2-(4,5-diphenyl-2oxazolyl)ethyl]phenoxy]acetate (5 g, 12 mmold), 5N sodium hydroxide solution (7.26 mL) and methanol (100 mL) was heated on a steam bath for 45 minutes. The solution was concentrated in vacuo diluted with water and 2N HCl solution an a white solid filtered off. Recrystallization from methanol gave 2-[4-[2-(4,5-diphenyl-2-oxazolyl)ethyl]phenoxy]acetic acid (2.88 g, 59%), m.p. 147°-149° C.

Anal. Calcd. for $C_{25}H_{21}NO_4$: C, 75.17; H, 5.30; N, 3.51. Found: C, 75.03; H, 5.50; N, 3.44%.

$^1$H-NMR (DMSO-d$^6$) delta: 3.11 (4H, bs), 4.68 (2H, s), 6.90 (2H, bs), 7.24 (2H, d, J=6 Hz), 7.30 to 7.90 (10H, m) and 13.10 (1H, bs).

EXAMPLE 9

Ethyl 3-[3-[2-(4,5-diphenyl-2-oxazolyl)ethyl]phenyl-2-propenoate

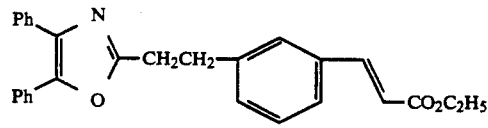

A mixture of 3-[2-(4,5-diphenyl-2-oxazolyl)ethyl]-phenyltrifluoromethane sulfonate (11.8 g, 25 mmol), ethyl acrylate (5.01 g, 50 mmol), triethylamine (10.12 g, 100 mmol) palladium II acetate (0.28 g, 1.25 mmol) 1,3-bis-(diphenylphosphine)propane (0.52 g, 1.25 mmol) and DMF (100 mL) was stirred at 90° C. under an atmosphere of nitrogen. After 2 hours and 6 hours additional palladium II acetate (0.28 g, 1.25 mmol) and 1,3-bis-(diphenylphosphine)propane (0.52 g, 1.25 mmol) was added. After 22 hours, the mixture was diluted with water and extracted with ethyl acetate. The combined extracts were washed three times with water and once with saturated sodium chloride solution, dried over sodium sulfate and concentrated. The residual oil was chromatographed on a column of silica gel using a mixture of hexanes and ethyl acetate (3:1) as eluent to give ethyl 3-[3-[2-(4,5-diphenyl-2-oxazolyl)ethyl]phenyl-2-propenoate (9.37 g, 88%) as an oil.

Anal. Calcd. for $C_{28}H_{25}NO_3$: C, 79.41; H, 5.96; N, 3.31. Found: C, 79.20; H, 6.21; N, 3.45%.

$^1$H-NMR ($CDCl_3$) delta: 1.31 (3H, t, J=7 Hz), 3.17 (4H, m), 4.24 (2H, q, J=7 Hz), 6.41 (1H, d, J=16 Hz), 7.20 to 7.50 (10 H, m) and 7.50 to 7.80 (5H, m).

EXAMPLE 10

3-[3-[2-(4,5-Diphenyl-2-oxazolyl)ethyl]phenyl]-2-propenoic acid hydrate hexane solvate

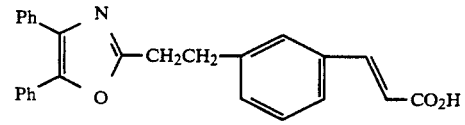

A mixture of ethyl 3-[3-[2-(4,5-diphenyl-2-oxazolyl)ethyl]phenyl]-2-propenoate (1.50 g, 3.5 mmol), 3N sodium hydroxide solution (3.5 mL) and methanol (100 mL) was heated on a steam bath. After 25 minutes the mixture was cooled, concentrated, diluted with water and made pH=1 with dilute hydrochloric acid solution. The mixture was extracted three times with $CH_2Cl_2$. The combined extracts were washed with saturated NaCl solution, dried over sodium sulfate and the solvent evaporated. The residual oil was chromatographed on a column of silica gel using a mixture of chloroform and methanol (9:1) as eluent to give 3-[3-[2-(4,5-diphenyl-2-oxazolyl)ethyl]phenyl]-2-propenoic acid (1.40 g, 100%) as the hydrated hexane solvate after recrystallization from a mixture of hexanes and $CH_2Cl_2$ (3:1), mp 114°-115° C.

Anal. Calcd. for $C_{26}H_{21}NO_3.0.6C_6H_{14}$ $0.2H_2O$: C, 78.88; H, 6.67; N, 3.11; $H_2O$, 0.70. Found: C, 78.54; N, 6.86; N, 3.04; $H_2O$, 0.21%.

---

Evaporation of the solvent left a beige solid, sodium 2-[3-[2-(4,5-diphenyl-2-oxazolyl]ethyl]phenoxy]acetate (1.06 g, 100%) m.p. 278°-280°C.

Anal. Calcd. for $C_{25}H_{20}NO_4Na.0.2H_2O$: C, 70.65; H, 4.84; N, 3.30; $H_2O$, 0.85. Found: C, 70.46; H, 4.75; N, 3.23; $H_2O$, 0.68%.

$^1$H-NMR ($D_2O$) delta: 2.55 (4H, bs), 4.19 (2H, s), 6.20 (1H, d, J=7.5 Hz), 6.45 to 6.70 (5H, m), 6.79 (1H, t, J=7.5 Hz), 6.90 to 7.30 (7H, m).

$^1$H-NMR (CDCl$_3$) delta: 0.86 (3H, t, J=7 Hz), 1.25 (4H, m), 3.19 (4H, s) 6.44 (1H, d, J=16 Hz), 7.25 to 7.70 (14H, m) and 7.75 (1H, d, J=16 Hz).

EXAMPLE 11

Ethyl 3-[2-(4,5-diphenyl-2-oxazolyl)ethyl]benzenepropanoate

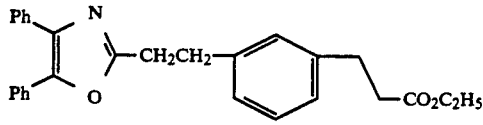

A solution of ethyl 3-[2-(4,5-diphenyl-2oxazolyl)-ethyl]phenyl-2-propenoate (1.02 g, 2.4 mmol) in ethyl acetate (50 mL) was hydrogenated over 10% palladium on charcoal (0.06 g) at 35 psi. After 27 hours, the mixture was filtered, concentrated and the residue subjected to chromatography on a column of silica gel using a mixture of ethyl acetate and hexanes (9:1) as eluent. Elution gave ethyl 3-[2-(4,5-diphenyl-2-oxazolyl)ethyl]benzene propanoate (0.92 g, 90%) as an oil.

Anal. Calcd. for C$_{28}$H$_{27}$NO$_3$: C, 79.04; H, 6.40; N, 3.30. Found: C, 79.12; H, 6.72; N, 3.30%.

$^1$H-NMR (CDCl$_3$) delta: 1.22 (3H, t, J=7 Hz), 2.59 (2H, t, J=8 Hz), 2.93 (2H, t, J=8 Hz), 3.14 (4H, s), 4.11 (2H, q, J=7 Hz), 7.00 to 7.50 (10H, m) and 7.50 to 7.70 (4H, m).

EXAMPLE 12

3-[2-(4,5-Diphenyl-2-oxazolyl) ethyl]benzenepropanoic acid

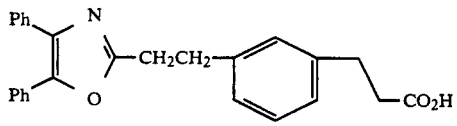

A mixture of ethyl 3-[2-(4,5-diphenyl-2-oxazolyl)ethyl]benzenepropanoate (1.85 g, 4.3 mmol), 3N sodium hydroxide solution (4.4 mL) and methanol (100 mL) was heated on a steam bath. After 20 minutes the mixture was concentrated, diluted with water and 1N hydrochloric acid solution to pH=1 and extracted with CH$_2$Cl$_2$. The combined extracts were dried over sodium sulfate and the solvent evaporated to leave a white solid. Recrystallization from a mixture of hexanes and CH$_2$Cl$_2$ gave 3-[2-(4,5-diphenyl-2-oxazolyl)ethyl]benzenepropanoic acid (1.58 g, 91%) mp 119°-120° C.

Anal. Calcd. for C$_{26}$H$_{23}$NO$_3$: C, 78.57; H, 5.84; N, 3.53. Found: C, 78.61; H, 5.96; N, 3.31%.

$^1$H-NMR (CDCl$_3$) delta: 2.64 (2H, t, J=8 Hz), 2.93 (2H, t, J=7 Hz), 3.14 (4H, s), 7.05 to 7.50 (10H, m) and 7.50 to 7.75 (4H, m).

EXAMPLE 13

Methyl [3-[2-(4,5-diphenyl-2-oxazolyl)ethenyl]phenoxy]acetate

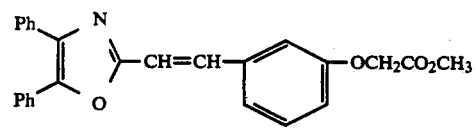

Sodium metal (260 mg, 11 mg atom) was dissolved in methanol (50 mL) and dimethyl [(4,5-diphenyl-2-oxazolyl)methyl]phosphonate (3.89 g, 11 mmol) added followed by methyl (3-formylphenoxy)acetate (2 g, 10 mmol). The mixture was stirred at room temperature for 20 minutes before being concentrated and diluted with 2N HCl solution. The mixture was extracted with CH$_2$Cl$_2$, the organic phase dried over sodium sulfate and the solvent evaported to leave a yellow oil. This was combined with the crude material from a reaction performed on 2 g of the phosphonate and 985 mg of aldehyde and chromatographed on a column of silica gel. Elution with a mixture of hexanes and diethyl ether (3:2) furnished methyl [3-[2-(4,5-diphenyl-2-oxazolyl)ethenyl]phenoxy]acetate as the diethyl ether solvate (2.92 g, 46%) after recrystallization from diethyl ether, m.p. 79°-82° C.

Anal. Calcd. for C$_{26}$H$_{21}$NO$_4$.0.3C$_4$H$_{10}$O: C, 75.34; H, 5.58; N, 3.23. Found: C, 75.35; H, 5.47; N, 3.17%.

$^1$H-NMR (CDCl$_3$) delta: 1.26 (1.25H, t, J=7 Hz), 3.53 (0.75 H, q, J=7 Hz), 3.88 (3H, s), 4.73 (2H, s), 6.94 (1H, dd, J=7.5 Hz, J'=2 Hz), 7.06 (1H, d, J=16 Hz), 7.14 (1H, t, J=2 Hz), 7.20 to 7.55 (8H, m), 7.60 (1H, d, J=16 Hz), and 7.70 to 7.90 (5H, m).

EXAMPLE 14

[3-[2-(4,5-Diphenyl-2-oxazolyl)ethenyl]phenoxy]acetic Acid

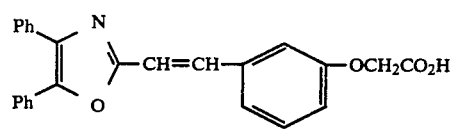

A mixture of methyl [3-[2-(4,5-diphenyl-2oxazolyl)ethenyl]phenoxy]acetate (1.00 g, 2.5 mmol), 5N sodium hydroxide solution (2 mL) and methanol (15 mL) was heated on a steam bath for 10 minutes before being concentrated. Dilution with water and 2N HCl solution gave a yellow solid which was combined with the crude product from a reaction performed on 1.46 g of ester using 3 mL of 5N NAOH in 40 mL methanol. Recrystallization from ethanol gave [3-[2-(4,5-diphenyl-2-oxazolyl)ethenyl]phenoxy]acetic acid (1.70 g, 70%), m.p. 213°-215° C.

Anal. Calcd. for C$_{25}$H$_{19}$NO$_4$: C, 75.56; H, 4.82; N, 3.53. Found: C, 75.37; H, 4.87; N, 3.43%.

$^1$H-NMR (DMSO-d$^6$) delta: 4.75 (2H, s), 6.90 (1H, m), 7.20 to 7.70 (13H, m) and 13.02 (1H, bs).

EXAMPLE 15

Methyl [4-[2-(4,5-diphenyl-2-oxazolyl)ethenyl]phenoxy]acetate

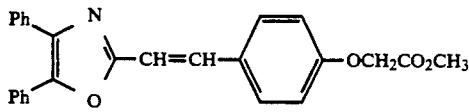

Sodium metal (570 mg, 25 mg atom) was dissolved in methanol (50 mL) and dimethyl [(4,5-diphenyl-2-oxazolyl)methyl]phosphonate (7.80 g, 22 mmol) added. The mixture was stirred for 10 minutes before adding methyl (4-formylphenoxy)acetate (4.00 g, 20 mmol). After stirring at room temperature for 1 hour, the mixture was diluted with water and a yellow solid filtered off and air dried to give crude product (3.80 g, 44%). This was combined with 3.50 g from a previous experiment and recrystallized twice from methanol to afford analytically pure methyl [4-[2-(4,5-diphenyl-2-oxazolyl)ethenyl]phenoxy]acetate, m.p. 122°–123° C.

Anal. Calcd. for $C_{26}H_{21}NO_4$: C, 75.90; H, 5.15; N, 3.41. Found: C, 76.00; H, 5.16; N, 3.44%.

H-NMR (DMSO-$d^6$) delta: 3.70 (3H, s), 4.85 (2H, s), 6.97 (2H, d, J=10 Hz), 7.08 (1H, d, J=13.5 Hz), 7.30 to 7.55 (6H, m), and 7.55 to 7.80 (7H, m).

EXAMPLE 16

[4-[2-(4,5-Diphenyl-2-oxazolyl)-ethenyl]phenoxy]acetic Acid

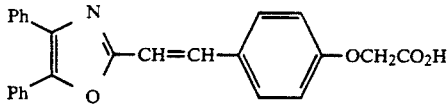

A mixture of methyl [4-[2-(4,5-diphenyl-2-oxazolyl)ethenyl]phenoxy]acetate (2.00 g, 5 mmol), 5N sodium hydroxide solution (2.90 mL), water (40 mL) and methanol (10 mL) was heated on a steam bath to give a solution. The mixture was cooled, diluted with 2N hydrochloric acid solution to pH=1 and filtered. Recrystallization from ethanol gave [4-[2-(4,5-diphenyl-2-oxazolyl)ethenyl]acetic acid (1.34 g, 69%), m.p. 223°–225° C.

Anal. Calcd. for $C_{25}H_{19}NO_4$: C, 75.56; H, 4.82; N, 3.53. Found: C, 75.47; H, 4.79; N, 3.55%.

$^1$H-NMR (DMSO-$d_6$) delta: 4.74 (2H, s), 6.95 (2H, d, J=8.5 Hz), 7.08 (1H, d, J=16 Hz), 7.20 to 7.50 (6H, m), 7.50 to 7.70 (5H, m), 7.69 (2H, d, J=8.5 Hz), and 13.08 (1H, bs).

EXAMPLE 17

Methyl 3-[3-[(4,5-diphenyl-2-oxazolyl)methoxy]phenyl]propanoate

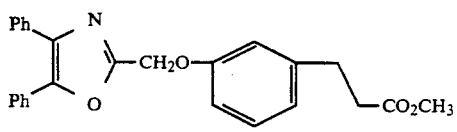

A mixture of 2-bromomethyl-4,5-diphenyloxazole (10.00 g, 3 mmol), methyl 3-(3-hydroxyphenyl)propanoate (5.73 g, 3 mmol) potassium carbonate (4.83 g, 3.5 mmol) potassium iodide (catalytic amount) and acetonetrile (150 mL) was stirred at reflux temperature. After 30 minutes, the mixture was filtered, concentrated in vacuo and the residual oil chromatographed on a column of silica gel. Elution with a mixture of hexanes and diethyl ether (3:1) furnished methyl 3-[3-((4,5-diphenyl-2-oxazolyl)methoxy]phenyl]propanoate (10.34 g, 78%) as an oil. An analytical sample was prepared by subjecting a 4 g sample to chromatography under the conditions described above to furnish pure material as an oil.

Anal. Calcd. for $C_{26}H_{23}NO_4$: C, 75.53; H, 5.61; N, 3.39. Found: C, 75.11; H, 5.60; N, 3.33%.

$^1$H-NMR (CDCl$_3$) delta: 2.63 (2H, t, J=8 Hz), 2.95 (2H, t, J=8 Hz), 3.65 (3H, s), 5.19 (2H, s), 6.80 to 7.05 (3H, m), 7.20 to 7.55 (7H, m) and 7.60 to 7.80 (4H, m).

EXAMPLE 18

3-[3-[(4,5-Diphenyl-2-oxazolyl)methoxy]phenyl)]-propanoic Acid

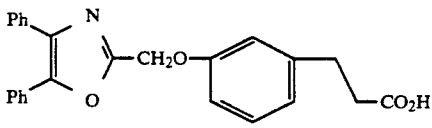

A mixture of methyl 3-[3-[(4,5-diphenyl-2-oxazolyl)methoxy]phenyl]propanoate (6 g, 14.5 mmol), 5N sodium hydroxide solution (8.7 mL) and methanol (150 mL) was heated to reflux on a steam bath. After 20 minutes the mixture was concentrated, diluted with water (200 mL) and 2N hydrochloric acid solution to pH=1. After filtration and drying in air overnight, the solid was recrystallized from a mixture of hexanes and CH$_2$Cl$_2$ to give 3-[3-[(4,5-diphenyl-2-oxazolyl)methoxy]phenyl]propanoic acid (4.15 g, 71%), m.p. 118°–120° C.

Anal. Calcd: for $C_{25}H_{21}NO_4 \cdot 0.11H_2O$: C, 74.84; H, 5.33; N, 3.50; H$_2$O, 0.45. Found: C, 74.49; H, 5.31; N, 3.31; H$_2$O, 0.05%.

$^1$H-NMR (CDCl$_3$) delta: 2.67 (2H, t, J=8 Hz), 2.95 (2H, t, J=8 Hz), 5.22 (2H, s), 6.80 to 7.00 (3H, m), 7.15 to 7.50 (7H, m), 7.55 to 7.80 (4H, m) and 10.71 (1H, bs).

EXAMPLE 19

Methyl 3-[4-[(4,5-diphenyl-2oxazolyl)methoxy]phenyl]-propanoate

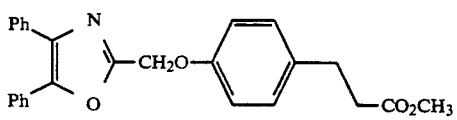

Reaction of 2-bromomethyl-4,5-diphenyloxazole and methyl 3-(4-hydroxyphenyl)propanoate according to the procedure of Example 17 provided the title compound, m.p. 92°–95° C.

Anal. Calcd. for $C_{26}H_{23}NO_4 \cdot 0.3H_2O$: C, 74.56; H, 5.68; N, 3.35; H$_2$O, 1.29. Found: C, 74.37; H, 5.81; N, 2.81; H$_2$O, 0.13.

EXAMPLE 20

3-[4-[(4,5-Diphenyl-2-oxazolyl)methoxy]phenyl]-propanoic Acid

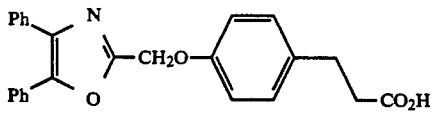

Methyl 3-[4-[(4,5-diphenyl-2-oxazolyl)methoxy]phenyl]propanoate was hydrolyzed with aqueous sodium hydroxide according to the procedure of Example 18 to provide the title compound, m.p. 124°–127° C.

Anal. Calcd. for $C_{25}H_{21}NO_4$: C, 75.18; H, 5.30; N, 3.51. Found: C, 74.73; H, 5.38; N, 3.49.

EXAMPLE 21

Methyl 3-[3-[(4,5-diphenyl-2-oxazolyl)methoxy]phenyl]-2-propenoate

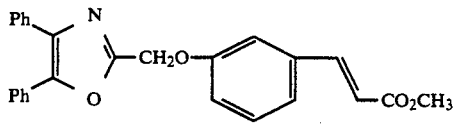

Sodium hydride (2.57 g of a 60% disp, 64 mmol) was washed with hexanes, covered with dimethylether (250 mL) and trimethyl phosphonoacetate (10.71 g, 9.52 mL, 59 mmol) added portionwise. The mixture was stirred for 15 minutes and a solution of 3-[(4,5-diphenyl-2-oxazolyl)methoxy]benzaldehyde (19.00 g, 53 mmol) in dimethylformamide (50 mL) added in one portion. The mixture was stirred for 30 minutes to give an amber solution before being diluted with water and extracted with $CH_2Cl_2$. The combined extracts were dried over sodium sulfate and the solvent evaporated to leave an oil that crystallized upon trituration with a mixture of hexanes and diethyl ether to give methyl 3-[3-(4,5-diphenyl-2-oxazolyl)-methoxy]phenyl]-9-propenoate (27.20 g, 78%). An analytical sample was prepared by recrystallising 1.40 g from ʹPrOH to give 0.85 g of pure material mp 88°–90° C.

Anal. Calcd. for $C_{26}H_{21}NO_4$: C, 75.90; H, 5.15; N, 3.41. Found: C, 75.80; H, 5.18; N, 3.43%.

$^1$H-NMR (CDCl$_3$) delta: 3.85 (3H, s), 5.27 (2H, s), 6.49 (1H, d, J=16 Hz), 7.10 to 7.55 (10H, m) and 7.60 to 7.80 (5H, m).

EXAMPLE 22

3-[3-[(4,5-Diphenyl-2-oxazolyl)-methoxy]phenyl]-2-propenoic acid

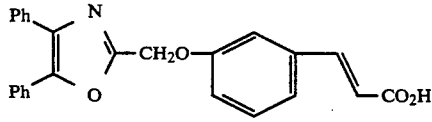

A mixture of methyl 3-[3-[(4,5-diphenyl-2-oxazolyl)-methoxy]phenyl]-2-propenoate (3 g, 7.2 mmol), 5N sodium hydroxide solution (4.40 mL) and methanol (60 mL) was heated to reflux. After 30 minutes, the mixture was cooled, concentrated, diluted with water and acidified to pH=1 with 2N hydrochloric acid solution. A yellow solid was filtered off and recyrstallised from a mixture of hexanes and $CH_2Cl_2$ to give 3-[3-[(4,5-diphenyl-2-oxazolyl)methoxy]phenyl]-2-propenoic acid (2.25 g, 77%), mp 145°–147° C.

Anal. calcd. for $C_{25}H_{19}NO_4.0.1H_2O$: C, 75.22; H, 4.85; N, 3.51; $H_2O$, 0.45. Found: C, 74.94; H, 4.86; N, 3.42; $H_2O$, 0.11%.

$^1$H-NMR (CDCl$_3$/DMSO-d$^6$) delta: 5.24 (2H, s), 6.46 (1H, d, J=16 Hz), 7.09 (1H, dd, J=8 Hz J'=2 Hz) 7.17 (1H, d, J=8 Hz), 7.25 (1H, d, J=2 Hz), 7.30 to 7.50 (7H, m) and 7.60 to 7.80 (5H, m).

EXAMPLE 23

Methyl 3-[4-[(4,5-diphenyl-2-oxazolyl)methoxy]phenyl]-2-propenoate

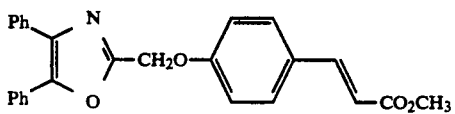

Reaction of trimethyl phosphonacetate and 4-[(4,5-diphenyl-2-oxazolyl)methoxy]benzaldehyde according to the procedure of Example 21 provided the title compound, m.p. 159°–161° C.

Anal. Calcd. for $C_{26}H_{21}NO_4.0.3H_2O$: C, 74.92; H, 5.23; N, 3.37; $H_2O$, 1.30. Found: C, 74.96; H, 5.04; N, 3.35; $H_2O$, 0.03.

EXAMPLE 24

3-[4-(4,5-Diphenyl-2-oxazolyl)-methoxy]phenyl]-2-propenoic Acid

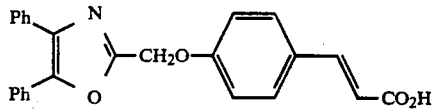

Methyl 3-[4-(4,5-diphenyl-2-oxazolyl)methoxy]phenyl]-2-propenoate was hydrolyzed with aqueous sodium hydroxide according to the procedure of Example 22 to provide the title compound, m.p. 205°–207° C.

Anal. Calcd. for $C_{25}H_{19}NO_4.0.1H_2O$: C, 75.22; H, 4.85; N, 3.51; $H_2O$, 0.45. Found: C, 75.14; H, 4.86; N, 3.47; $H_2O$, 0.20.

EXAMPLE 25

Methyl [3-[(4,5-diphenyl-2-oxazolyl)methoxy]phenoxy]acetate

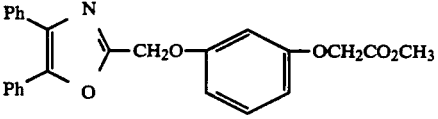

A mixture of 2-bromomethyl-4,5-diphenyloxazole (6.68 g, 21 mmol), methyl (3-acetoxyphenoxy)acetate (3.87 g, mmol), potassium carbonate (3.52 g, 25 mmol), potassium iodide (catalytic amount) and acetonitrile (125 mL) was stirred at reflux. After 40 minutes, the mixture was cooled, filtered and the solvent evaporated to leave an oil. Chromatography on a column of silica gel using a mixture of hexanes and diethyl ether (3:1) as eluent furnished hydrated methyl[3-[4,5-diphenyl-2- oxazolyl)methoxy]phenoxy]acetate (6.45 g, 72%) as an oil.

Anal. Calcd. for C$_{25}$H$_{21}$NO$_5$.0.2H$_2$O: C, 71.66; H, 5.15; N, 3.35; H$_2$O, 0.86. Found: C, 71.56; H, 5.49; N, 3.44; H$_2$O, 0.60%.

$^1$H-NMR (CDCl$_3$) delta: 3.77 (3H, s), 4.61 (2H, s), 5.17 (2H, s), 6.55 (1H, dd, J=8 Hz J$^1$=2 Hz), 6.65 (1H, m), 6.72 (1H, dd, J=8 Hz, J'=2 Hz), 7.20 (1H, t, J=8 Hz), 7.30 to 7.50 (6H, m), and 7.50 to 7.70 (4H, m).

EXAMPLE 26

[3-[(4,5-Diphenyl-2-oxazolyl)methoxy]phenoxy]acetic acid

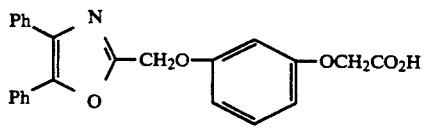

A mixture of methyl [3-[(4,5-diphenyl-2-oxazolyl)methoxy]phenoxy acetate (5.85 g, 14 mmol), 5N sodium hydroxide solution (8.45 mL) and methanol (100 mL) was heated to reflux. After 10 minutes, the mixture was cooled, the solvent evaporated and the residue diluted with water and 2N HCl solution to pH=1. A yellow solid was filtered off and recrystallized from a mixture of chloroform, diethyl ether, methanol and hexanes to give hydrated 3-[(4,5-diphenyl-2-oxazolyl)methoxy]phenoxy]acetic acid (2.70 g, 47%), mp 133°–135° C.

Anal. Calcd. for C$_{24}$H$_{19}$NO$_5$.0.6H$_2$O: C, 69.93; H, 4.94; H, 3.40; H$_2$O 2.62. Found: C, 69.61; H, 4.79; N, 3.35; H$_2$O, 0.21%.

$^1$H-NMR (DMSO-d$^6$) delta: 4.47 (2H, s), 5.29 (2H, s), 6.54 (1H, d, J=8 Hz), 6.68 (2H, m), 7.20 (1H, t, J=8 Hz), 7.30 to 7.80 (14H, m).

EXAMPLE 27

Ethyl 3-[3-[2-(4,5-diphenyl-2-oxazolyl)ethenyl]phenyl]-2-propenoate

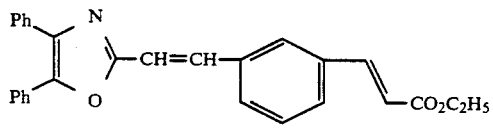

Reaction of 3-[2-(4,5-diphenyl-2-oxazolyl)ethenyl]phenyltrifluoromethane sulfonate obtained by reaction of trifluoromethanesulfonic anhydride with 3-[2-(4,5-diphenyl-2-oxazolyl)ethenyl]phenol according to the procedure of Example 37 and ethyl acrylate analogously to the procedure of Example 9 provides the title compound.

EXAMPLE 28

3-[3-[2-(4,5-Diphenyl-2-oxazolyl)ethenyl]phenyl]-2-propenoic Acid

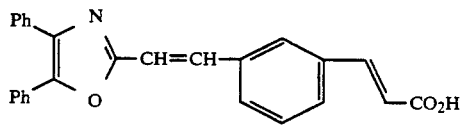

Hydrolysis of ethyl 3-[3-[2-(4,5-diphenyl-2-oxazolyl)ethenyl]phenyl]-2-propenoate with sodium hydroxide analogously to the procedure of Example 10 provides the title compound.

EXAMPLE 29

Methyl [3-[2-[4,5-di(3-thienyl)-2-oxazolyl]ethyl]phenoxy]acetate

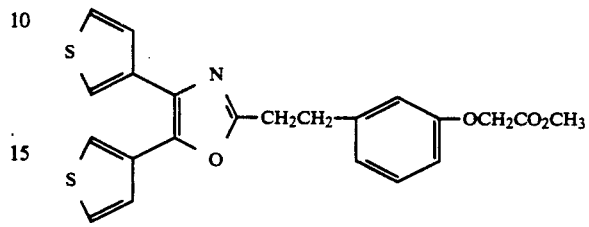

A mixture of 3-[2-[4,5-di(3-thienyl)-2-oxazolyl]ethyl]phenol (2.00 g, 5.6 mmol), methyl bromoacetate (1.04 g, 6.8 mmol), potassium carbonate (0.94 g, 6.8 mmol), potassium iodide (catalytic amount) and acetonitrile (100 mL) was stirred at reflux under an atmosphere of nitrogen. After 15 hours, the mixture was cooled, filtered and concentrated and the residue subjected to chromatography on a column of silica gel. Elution with a mixture of hexanes and ethyl acetate (7:2) gave methyl [3-[2-[4,5-di(3-thienyl)-2-oxazolyl]ethyl]phenoxy]acetate (1.95 g, 80%) as an oil.

Anal. Calcd. for C$_{22}$H$_{19}$NO$_4$S$_2$: C, 62.10; H, 4.51; N, 3.30. Found: C, 62.39; H, 4.64; N, 3.37%.

$^1$H-NMR (CDCl$_3$) delta: 3.10 (4H, s), 3.78 (3H, s), 4.60 (2H, s), 6.74 (1H, dd, J=8 Hz, J'=2.5 Hz), 6.81 (1H, bs), 6.89 (1H, d, J=8 Hz), 7.10 to 7.40 (5H, m), and 7.50 to 7.70 (2H, m).

EXAMPLE 30

[3-[2-[4,5-Di(3-thienyl)-2-oxazolyl]ethyl]phenoxy]acetic acid

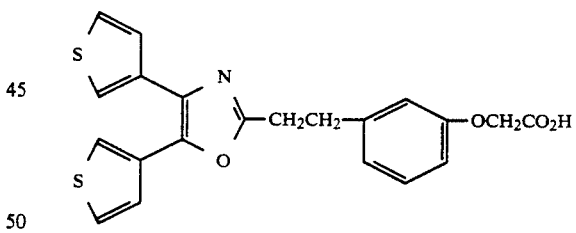

A mixture of methyl [3-[2-[4,5-di(3-thienyl)-2-oxazolyl]ethyl]phenoxy]acetate (1.40 g, 3.3 mmol), 3N sodium hydroxide solution (3.3 mL) and methanol (50 mL) was heated on a steam bath for 20 minutes. The solvent was evaporated, the residue diluted with water and 1N HCl solution until pH=1 and extracted with CH$_2$Cl$_2$. The combined extracts were dried over sodium sulfate and concentrated to give a beige solid. Recrystallization from a mixture of hexanes and CH$_2$Cl$_2$ (5:3) afforded hydrated [3-[2-[4,5-di(3-thienyl)-2-oxazolyl]ethyl]phenoxy]acetic acid (1.16 g, 85%), mp 154°–156° C.

Anal. Calcd. for C$_{21}$H$_{17}$NO$_4$S$_2$.0.4H$_2$O: C, 60.25; H, 4.29; N, 3.35; H$_2$O, 1.72. Found: C, 60.11; H, 4.20; N, 3.26; H$_2$O, 1.06%.

$^1$H-NMR (DMSO-d$^6$ delta: 3.06 (4H, m), 4.61 (2H, S), 6.72 (1H, dd, J=8 Hz, J'=2.5 Hz), 6.87 (2H, m), 7.17

(1H, t, J=8 Hz), 7.25 (2H, m), 7.60 to 7.90 (4H, m) and 13.03 (1H, bs).

EXAMPLE 31

Methyl [3-[2-[4,5-di(2-thienyl)-2-oxazolyl]ethyl]phenoxy]acetate

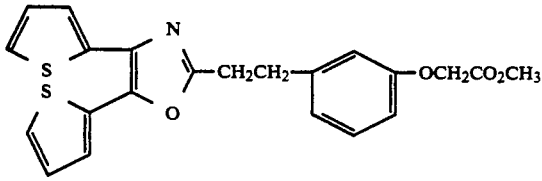

Reaction of 3-[2-[4,5-di(2-thienyl)-2-oxazolyl]-ethyl]-phenol with methyl bromoacetate according to the procedure of Example 29 provided the title compound.

EXAMPLE 32

[3-[2-[4,5-Di(2-thienyl)-2-oxazolyl]ethyl]phenoxyacetic Acid

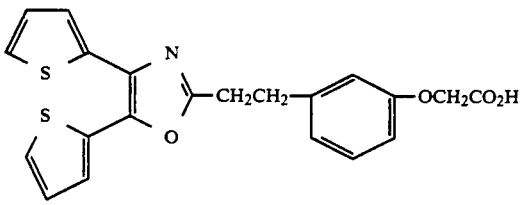

Hydrolysis of methyl [3-[2-[4,5-di(2-thienyl)-2-oxazolyl]ethyl]phenoxy]acetate with aqueous sodium hydroxide provided the hydrated title compound, m.p. 105.5°–107° C.

Anal. Calcd. for $C_{21}H_{17}NO_4S_2 \cdot 0.3H_2O$: C, 60.51; H, 4.26; N, 3.36; $H_2O$, 1.29. Found: C, 60.40; H, 4.29; N, 2.95; $H_2O$, 1.26.

EXAMPLE 33

Preparation of Scheme I Intermediates (33-1)

2-Oxo-1,2-diphenylethyl-8-bromooctanoate

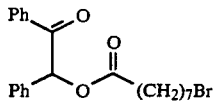

A mixture of benzoin (10 g, 47 mmol), 8-bromooctanoic acid (11.57 g, 52 mmol), 1,3-dicyclohexylcarbodiimide (11.66 g, 57 mmol), 4-dimethylaminopyridine (catalytic amount) and dichloromethane (250 mL) was stirred at room temperature under an atmosphere of nitrogen. After 17 hours, the mixture was filtered and concentrated to leave an oil which was chromatographed on a column of silica gel. Eluting with a mixture of hexanes and diethyl ether (9:1) afforded 2-oxo-1,2-diphenylethyl-8-bromooctanoate (18.43 g, 93%). A 1 g sample was rechromatographed providing analytically pure material, m.p. 58°–62° C.

Anal. Calcd. for $C_{22}H_{25}BrO_3$: C, 63.32; H, 6.04. Found: C, 63.39; H, 5.88%.

$^1$H-NMR (CDCl$_3$) delta: 1.20 to 1.45 (6H, m), 1.67 (2H, quintet, J=7 Hz), 1.82 (2H, quintet, J=7 Hz), 2.46 (2H, m), 3.37 (2H, t, J=7 Hz), 6.86 (1H, s), 7.30 to 7.55 (8H, m), 7.92 (2H, d, J=7.5 Hz).

(33-2)

2-(7-Bromoheptyl)-4,5-diphenyloxazole

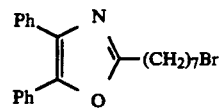

A solution of 2-oxo-1,2-diphenylethyl-8-bromooctanoate (16.0 g, 38 mmol), and ammonium acetate (14.8 g, 19.2 mmol) in acetic acid (240 mL) was heated at reflux. After 1 hour, the mixture was poured onto water and extracted with CH$_2$Cl$_2$ (3×). The combined extracts were washed with water, dried over sodium sulfate and concentrated in vacuo to leave an oil. Chromatography on a column of silica gel using a mixture of hexanes and diethyl ether (9:1) as eluent afforded 2-(7-bromoheptyl)-4,5-diphenyloxazole (13.20 g, 86%). A 1 g sample was rechromatographed under identical conditions to provide analytically pure material as an oil.

Anal. Calcd. for $C_{22}H_{24}BrNO$: C, 66.34; H, 6.08; N, 3.52. Found: C, 66.36; H, 6.07; N, 7.38%.

$^1$H-NMR (CDCl$_3$) delta: 1.30 to 1.60 (6H, m), 1.80 to 1.95 (4H, m), 2.84 (2H, t, J=7.5 Hz), 3.38 (2H, t, J=7 Hz), 7.20 to 7.40 (6H, m) and 7.50 to 7.80 (4H, m).

(33-3)

Dimethyl 2-[7-(4,5-diphenyl-2-oxazolyl)heptyl]propanedioate

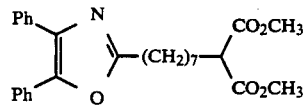

A mixture of 2-(7-bromoheptyl)-4,5-diphenyloxazole (10.00 g, 25 mmol), dimethyl malonate (9.95 g, 8.60 mL, 75 mmol), potassium tert-butoxide (8.44 g, 75 mmol), Eighteen Crown 6 ether (catalytic amount) and tetrahydrofuran (200 mL) was heated to reflux under an atmosphere of nitrogen. After 17.5 hours, the mixture was cooled, diluted with 2N hydrochloric acid solution and extracted with CH$_2$Cl$_2$. The combined extracts were dried over sodium sulfate and concentrated in vacuo to leave an oil. Chromatography on a column of silica gel using a mixture of hexanes and diethyl ether (9:1) as eluent afforded dimethyl 2-[7-(4,5-diphenyl-2-oxazolyl)-heptyl]propanedioate (9.47 g, 83%) as an oil. An analytical sample (hydrated) was prepared by rechromatographing a 3.28 g sample on silica gel using a mixture of hexane and diethyl ether (4:1) as the mobile phase.

Anal. Calcd. for $C_{27}H_{31}NO_5 \cdot 0.1\ H_2O$: C, 71.86; H, 6.97; N, 3.11; H$_2$O, 0.40. Found: C, 71.70; H, 7.26; N, 3.01; H$_2$O, 0.48%.

$^1$H-NMR (CDCl$_3$) delta: 1.20 to 1.50 (8H, m), 1.70 to 1.90 (4H, m), 2.80 (2H, t, J=7.5 Hz), 3.33 (1H, t, J=7.5 Hz), 3.33 (1H, t, J=7.5 Hz), 3.68 (6H, s); 7.20 to 7.40 (6H, m), and 7.50 to 7.70 (4H, m).

(33-4)

2-[7-(4,5-Diphenyl-2-oxazolyl)heptyl]propanedioic Acid

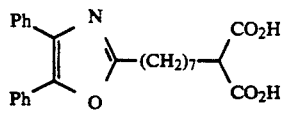

A mixture of dimethyl 2-[7-(4,5-diphenyl-2-oxazolyl)-heptyl]propanedioate (6.00 g, 13 mmol), 5N sodium hydroxide solution (13.4 mL), water (120 mL) and methanol (20 mL) was stirred at room temperature. After 10 minutes, the mixture was heated to reflux for 1 hour before adding water (80 mL,) and 5N NAOH solution (13 mL). After a further 3 hours at reflux, the mixture was cooled, acidified with 2N HCl solution and extracted with diethyl ether. The combined extracts were dried over sodium sulphate and the solvent evaporated to leave a white solid, 2-[7-(4,5-diphenyl-2-oxazolyl)heptyl]propanedioic acid (5.65 g, 100%). An analytical sample was prepared by recrystallizing 1.15 g from a mixture of $CH_2Cl_2$, diethyl ether and hexane to give pure product (1.05 g), m.p. 115°–117° C.

Anal. Calcd. for $C_{25}H_{27}NO_5$: C, 71.25; H, 6.46; N, 3.33. Found: C, 71.03; H, 6.49; N, 3.27%.

$^1$H-NMR (DMSO-$d^6$) delta: 1.10 to 1.45 (8H, m), 1.60 to 1.85 (4H, m), 2.78 (2H, t, J=7.5 z), 3.18 (1H, t, J=7.5 Hz), 7.25 to 7.50 (6H, m), 7.50 to 7.60 (4H, m) and 12.64 (2H, bs).

EXAMPLE 34

Preparation of Scheme 2 Intermediates

(34-1)

3-[3-Hydroxyphenyl)propionic Acdi

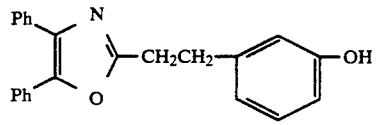

A solution of 3-hydroxycinnamic acid (20.00 g, 122 mmol) in methanol (200 mL) was hydrogenated over 10% palladium on charcoal (1.25 g) at 45–50 psi using a Parr hydrogenation apparatus. After 4 hours, the mixture was filtered through Celite and the solvent evaporated to leave a tan-colored solid which was used without further purification.

$^1$H-NMR (CD$_3$OD) delta: 2.32 (2H, t, J=7.5 Hz), 2.68 (2H, t, J=7.5 Hz), 6.30 to 6.50 (3H, m), and 6.82 (1H, t, J=8.5 Hz).

(34-2)

3-[2-(4,5-Diphenyl-2-oxazolyl)ethyl]phenol

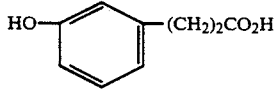

Sodium metal (2.69 g, 0.12 g atom) was dissolved in absolute ethanol (250 mL) and a solution of 3-(3-hydroxyphenyl)propionic acid (19.38 g, 120 mmol) in absolute ethanol (125 mL) added. The mixture was heated briefly to reflux, cooled and concentrated sulfuric acid (5 drops) in absolute ethanol (5 mL) added followed by 2-bromo-2-phenylacetophenone (32.11 g, 120 mmol). The mixture was stirred a reflux for 5.75 hours, cooled and concentrated in vacuo. To the residue was added glacial acetic acid (600 mL) and ammonium acetate (45.09 g, 0.58 mol) and the mixture heated at reflux for 10.5 hours. The cooled reaction mixture was partitioned between water and $CH_2Cl_2$, the organic phase separated, washed with water (3×) and saturated NaCl solution. After drying over sodium sulfate, evaporation of the solvent left a golden-colored solid. Recrystallization from a mixture of hexanes and $CH_2Cl_2$ (2:1) afforded 3-[2-(4,5-diphenyl)-2-oxazolyl)ethyl]phenol (29.35 g, 73%), m.p. 146°–147.5° C.

Anal. Calcd. for $C_{23}H_{19}NO_2.0.05H_2O$: C, 80.70; H, 5.63; N, 4.10; $H_2O$, 0.26. Found: C, 80.45; H, 5.69; N, 3.92; H 0.11%.

$^1$H-NMR (CDCl$_3$) delta: 3.05 (4H, m), 6.60 (2H, m), 6.68 (1H, d, J=7.5 Hz), 7.05 (1H, t, J=7.5 Hz), 7.20 to 7.45 (6H, m) and 7.50 to 7.80 (5H, m).

(34-3)

4-[2-4,5-Diphenyl-2-oxazolyl)ethyl]phenol

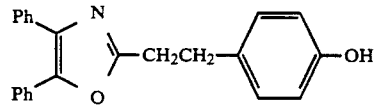

Sodium metal (1.00 g, 43 mg atom) was dissolved in ethanol (125 mL) and 3-(4-hydroxyphenyl)propionic acid (6.04 g, 36 mmol) added to give a white precipitate. The mixture was warmed briefly with stirring and concentrated $H_2SO_4$ (3 drops) added followed by 2-bromo-2-phenylacetophenone (1.00 g, 36 mmol). The mixture was heated at reflux for 2 hours, cooled, concentrated and diluted with water. The mixture was extracted with $CH_2Cl_2$, the combined extracts dried over sodium sulfate and concentrated to give an oil which was dissolved in acetic acid (250 mL). Ammonium acetate (14.00 g, 180 mmol) was added and the mixture heated to reflux. After 100 minutes, the solution was cooled, diluted with water and extracted with $CH_2Cl_2$. The combined extracts were dried over sodium sulfate and the solvent evaporated to leave a solid that was triturated with a mixture of hexanes and diethyl ether and filtered to give 4-[2-(4,5-diphenyl-2-oxazolyl)ethyl]phenol (8.00 g, 64%). An analytical sample was prepared by recrystallizing 1.5 g from a mixture of hexanes and $CH_2Cl_2$ to give 1.20 g of pure material, m.p. 142°–144° C.

Anal. Calcd. for $C_{23}H_{19}NO_4.0.1H_2O$: C, 80.50; H, 5.64; N, 4.04; $H_2O$, 0.53. Found: C, 80.16; H, 5.80; N, 4.16; $H_2O$, 0.06%.

$^1$H-NMR (CDCl$_3$) delta: 3.30 (4H, m), 6.80 (2H, d, J=8.5 Hz), 7.15 (2H, d, J=8.5 Hz), 7.35 to 7.70 (6H, m), 7.20 to 7.90 (4H, m) and 7.95 (1H, bs).

(34-4)

3-[2-(4,5-Diphenyl-2-oxazolyl)ethenyl]phenol

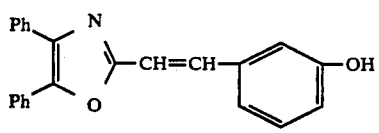

Sodium metal (1.68 g, 73 mg atom) was dissolved in ethanol (160 mL) and 3-hydroxycinnamic acid (10 g, 6 mmol) added. After stirring for 5 minutes, concentrated H₂SO₄ (4 drops) was added followed by 2-bromo-2-phenoxyacetophenone (16.76 g, 6 mmol) and the mixture heated to reflux. After 135 minutes, the mixture was cooled, diluted with water and extracted with CH₂Cl₂. The combined extracts were dried over sodium sulfate and concentrated to leave an oil which was dissolved in acetic acid (110 mL). Ammonium acetate (23.47 g, 300 mmol) was added and the mixture heated to reflux. After 75 minutes, the solution was cooled, diluted with water and extracted with CH₂Cl₂. The organic extracts were dried over sodium sulfate and the solvent evaporated to leave a khaki solid that was triturated with diethyl ether to give (10.80 g, 52%). Recrystallization of a 1.5 g sample from ethanol gave 0.7 g of analytically pure 3-[2-(4,5-diphenyl2-oxazolyl)ethenyl]phenol, m.p. 201°–203° C.

Anal. Calcd. for $C_{23}H_{17}NO_2$: C, 81.40; H, 5.05; N, 4.13. Found C, 81.02; H, 4.94; N, 3.93%.

¹H-NMR (DMSO-d⁶) delta: 6.77 (1H, d, J=7.5 Hz), 7.00 to 7.35 (4H, m), 7.35 to 7.50 (6H, m), 7.53 (1H, d, J=16 Hz), 7.60 to 7.70 (4H, m), and 9.58 (1H, s).

EXAMPLE 35

Preparation of Scheme 3 Intermediate Dimethyl[(4,5-diphenyl-2-oxazolyl)methyl]phosponate

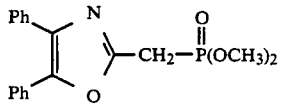

A mixture of 2-bromomethyl-4,5-diphenyloxazole (26.72 g, 85 mmol) obtained according to D. L. Aldous, et al., *J. Org. Chem.*, 25, 1151 (1960), and trimethylphosphite (80 g, 84 mL, 645 mmol) was heated with stirring at 120° C. under an atmosphere of nitrogen. After 90 minutes, the excess trimethyl phosphite was removed in vacuo and the residue chromatographed on a column of silica gel. Elution with a mixture of diethyl ether and methanol (49:1) afforded 6.13 g of a yellow solid and 18.90 g of an oil with identical TLC characteristics. Recrystallization of 1.3 g of the solid material from hexane provided analytically pure dimethyl [(4,5-dimethyl-2-oxazolyl)methyl]phosphonate 1.15 g, m.p. 54°–57° C.

Anal. Calcd. for $C_{18}H_{18}NO_4P$: C, 62.98; H, 5.29; N, 4.09. Found: C, 62.88; H, 5.26; N, 4.00%.

¹H-NMR (CDCl₃) delta: 3.48 (2H, d, J=21 Hz), 3.81 (6H, d, J=11 Hz), 7.20 to 7.35 (6H, m) and 7.50 to 7.70 (4H, m).

EXAMPLE 36

Preparation of Scheme 4 Intermediate 3-[(4,5-Diphenyl-2-oxazolyl)methoxy]benazldehyde

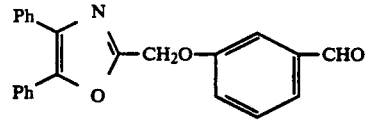

A mixture of 2-bromomethyl-4,5-diphenyloxazole (26.72 g, 85 mmol) obtained according to D. L. Aldous, et al., *J. Org. Chem.* 2, 228–334 (1937), 3-hydroxybenzaldehyde (9.34 g, 76 mmol), potassium carbonate (12.92 g, 93 mmol), potasssium iodide (0.5 g) and dimethylformamide (250 mL) was stirred at 110° C. After 45 minutes, the mixture was cooled, diluted with water and extracted with diethyl ether (3×). The combined extracts were washed with water (3×), dried over sodium sulfate and concentrated in vacuo to give an oil which was chromatographed on a column of silica gel. Elution with a mixture of hexanes and diethyl ether (2:1) afforded 3-[(4,5-diphenyl-2-oxazolyl)methoxy]benzaldehyde (21.16 g, 70%). An analytical sample was recrystallized from a mixture of CH₂Cl₂ and hexanes and had mp 72°–75° C.

Anal. Calcd. for $C_{23}H_{17}NO_3$: C, 77.74; H, 4.83; N, 3.95. Found: C, 77.49; H, 4.90; N 3.87%.

¹H-NMR (CDCl₃) delta: 5.28 (2H, S), 7.30 to 7.80 (14H, m) and 9.99 (1H, S).

EXAMPLE 37

Preparation of Scheme 5 Intermediate 3-[2-(4,5-Diphenyl-2-oxazolyl)ethyl]phenyltrifluoromethane sulfonate

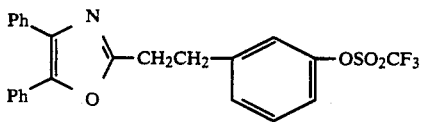

Trifluoromethanesulfonic anhydride (16.55 g, 58 mmol) was added to a stirred solution of 3-[2-(4,5-diphenyl-2-oxazolyl)ethyl]phenol (10.00 g, 29 mmol) in pyridine (60 mL) maintained at 0° C. The mixture was allowed to stand in the refrigerator overnight before being poured onto ice water and extracted with diethyl ether (3×). The combined extracts were washed four times with water, dried over anhydrous magnesium sulfate and concentrated to leave an oil. Chromatography on a column of silica gel using a mixture of hexanes and ethyl acetate (17:3) gave 3-[2-(4,5-diphenyl-2-oxazolyl)ethyl]phenyltrifluoromethane sulfonate (12.54 g, 90%) as an oil.

Anal. Calcd. for $C_{24}H_{18}F_3NO_4S$: C, 60.89; H, 3.84; N, 2.96. Found: C, 60.97; H, 3.93; N, 3.21%.

¹H-NMR (CDCl₃) delta: 3.18 (4H, m), 7.10 to 7.50 (10H, m) and 7.50 to 7.70 (4H, m).

EXAMPLE 38

Preparation of Scheme 6 Intermediate

Methyl (3-hydroxyphenoxy)acetate

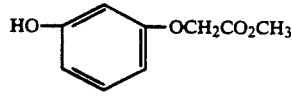

A mixture of resocirnol monoacetate (20.00 g, 0.13 mol), methyl bromoacetate (21.14 g, 13.05 mL, 0.14 mol), potassium carbonate (21.80 g, 0.16 mol) and acetonitrile (350 mL) was stirred ar reflux. After 30 minutes, the mixture was filtered, and the solvent removed in vacuo to leave an oil which was dissolved in methanol (350 mL). Concentrated hydrochloric acid (2 mL) was added and the mixture stirred at reflux. After 20 minutes, the solution was concentrated, diluted with water and extracted with $CH_2Cl_2$ to give an oil which was distilled at reduced pressure to furnish, methyl (3-hydroxyphenoxy)acetate, bp 154°–180° C./1.5 mm (15.98 g, 66%).

EXAMPLE 39

Preparation of Scheme 7 Intermediates (39-1)

2-[2-(3-[Dimethyl(1,1-dimethylethyl)siloxy]phenyl]ethyl]-4,5-di(3-thienyl)oxazole

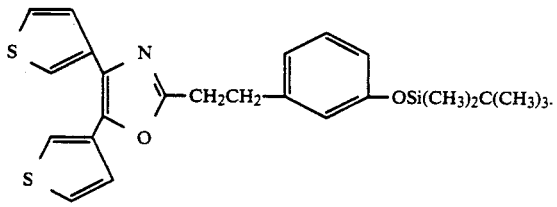

n-Butyllithium (0.518 g, 8 mmol) in hexanes (3.24 mL) was added to a solution of diisopropylamine (0.82 g, 8 mmol) in dry tetrahydrofuran (20 mL) maintained at 0° C. under an atmosphere of nitrogen. After 20 minutes, the mixture was cooled to −78° C. and a solution of 2-methyl-4,5-di(3-thienyl)oxazole (1.60 g, 6.5 mmol) obtained analogous to D. Davidson, et al., *J. Org. Chem*, 2, 328–334 (1937) in tetrahydrofuran (10 mL) added dropwise to give a red-orange solution. The mixture was stirred at −78° C. for 2 hours before adding a solution of [3-(bromomethyl)phenoxy]-dimethyl(1,1-dimethylethyl)silane (2.44 g, 8 mmol) in tetrahydrofuran (5 mL). After stirring at −78° C. for 4 hours, the mixture was Doured onto saturated ammonium chloride solution and extracted with diethyl ether. The combined extracts were washed twice with saturated ammonium chloride solution, once with saturated NaCl solution and dried over magnesium sulfate. The solvent was evaporated and the residue chromatographed on a column of silica gel using a mixture of hexanes and ethyl acetate (19:1) as eluent to give 2-[2-[3-[dimethyl(1,1-dimethylethyl)siloxy]phenyl]ethyl]4,5-di(3-thienyl)oxazole (1.33 g, 43%) as an oil.

$^1$H-NMR ($CDCl_3$) delta: 0.14 (6H, s), 0.94 (9H, s), 3.09 (4H, s), 6.70 (2H, m), 6.83 (1H, d, J=8 Hz), 7.13 (1H, t, J=8 Hz), 7.20 to 7.40 (4H, m) and 7.50 to 7.75 (2H, m).

(39-2)

3-[2-[4,5-Di(3-thienyl)-2-oxazolyl]ethyl]phenol

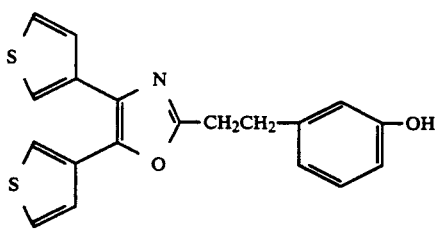

Tetra-n-butylammonium fluoride (2.98 g, 11 mmol) in tetrahydrofuran (11.40 mL) was added to a solution of 2-[2-[3-dimethyl(1,1-dimethylethyl)siloxy]phenyl]ethyl]-4,5-di(3-thienyl)oxazole (4.26 g, 9 mmol) in tetrahydrofuran (185 mL). The mixture was stirred at room temperature under an atmosphere of nitrogen. After 30 minutes, the mixture was diluted with diethyl ether and saturated ammonium chloride solution. The organic phase was separated, washed twice with saturated ammonium chloride solution and once with saturated NaCl solution before being dried over sodium sulfate and concentrated in vacuo. Chromatography of the residue on a column of silica using a mixture of hexanes and ethyl acetate (3:1) as eluent gave 3-[2-[4,5-di(3-thienyl)-2-oxazolyl]ethyl]phenol (2.45 g, 76%). An analytical sample was prepared by recrystallizing 0.45 g from a mixture of hexanes and $CH_2Cl_2$ (2:1) and had mp 143.5°–145° C.

Anal. Calcd. for $C_{19}H_{15}NO_2S_2$: C, 64.57; H, 4.28; N, 3.97. Found: C, 64.65; H, 4.41; N, 3.89%.

$^1$H-NMR (DMSO-$d^6$) delta: 3.00 (4H, m), 6.58 (1H, dd, J=8 Hz, J'=2 Hz), 6.67 (2H, m), 7.07 (1H, t, J=8 Hz), 7.25 (2H, m), 7.60 to 7.90 (4H, m) and 9.30 (1H, s).

EXAMPLE 40

5-[[3-[2-(4,5-Diphenyl-2-oxazolyl)-ethyl]phenoxy]methyl-1H-tetrazole

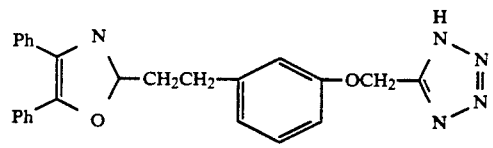

A mixture of 2-[3-[2-(4,5-diphenyl-2-oxazolyl)ethyl]phenoxy]acetonitrile (1.60 g, 4.2 mmol) and tri-n-butyltin azide (1.45 g, 4.4 mmol) was stirred at 140° C. under an atomosphere of nitrogen. After 20 hours, the mixture was cooled, diluted with ethyl acetate (300 mL) and 1N HCl (200 mL) and the mixture stirred for 2 hours. The aqueous phase was removed and the organic phase added to 0.1M potassium fluoride solution. After stirring overnight, the organic layer was separated, washed with water and saturated sodium chloride solution, dried over sodium sulfate and concentrated in vacuo. The residue was chromatographed on a column of silica gel using a mixture of chloroform and methanol (10:1) as eluent to give 5-[[3-[2-(4,5-diphenyl-2-oxazolyl)ethyl]phenoxy]methyl]-1H-tetrazole (1.18 g, 66%) after recrystallization from a mixture of hexanes and $CH_2Cl_2$ m.p. 138.5°–140° C.

Anal. Calcd. for $C_{25}H_{21}N_5O_2$: C, 70.91; H, 5.00; N, 16.54. Found: C, 70.83; H, 5.05; N, 16.49%.

$^1$H-NMR (CDCl$_3$+DMSO-d$^6$) delta: 2.91 (4H, s), 5.13 (2H, s), 6.55 to 6.70 (3H, m), 6.90 to 7.20 (7H, m) and 7.30 to 7.50 (4H, m).

SUPPLEMENTAL DISCLOSURE

The compounds of the instant invention are additionally characterized by Formula (XIX)

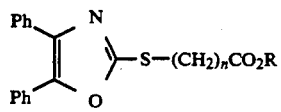
(XIX)

wherein n is 7–9 and R is hydrogen or lower alkyl; and Formula (XX)

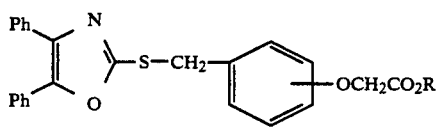
(XX)

wherein the OCH$_2$CO$_2$R moiety is attached to the 3 or 4 phenyl position and R is hydrogen or lower alkyl.

Formula XIX compounds are obtained by a process comprising:

(a) hydrolyzing a compound of Formula XXI

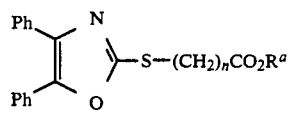
(XXI)

wherein n is 7–9 and R$^a$ is lower alkyl to the corresponding acid, or (b) esterifying a compound of Formula XXII

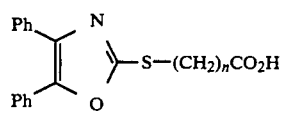
(XXII)

wherein n is 7–9 with a lower alkanol, or (c) alkylating 4,5-diphenyl-2(3H)oxazolethione with BR—(CH$_2$)$_n$CO$_2$R$^a$ wherein n is 7–9 and R$^a$ is lower alkyl.

Formula XX compounds are obtained by a process comprising:

(a) hydrolyzing a compound of Formula XXIII

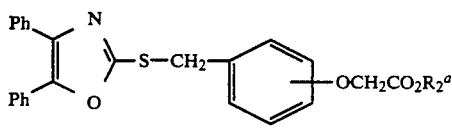
(XXIII)

wherein R$_2^a$ is lower alkyl and the OCH$_2$CO$_2$R moiety is attached to the 3 or 4 phenyl position, or (b) esterifying a compound of Formula XXIV

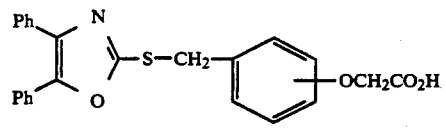
(XXIV)

wherein the OCH$_2$CO$_2$H moiety is attached to the 3 or 4 position with a lower alkanol, or (c) alkylating 4,5-diphenyl-2(3H)-oxazolethione with 3-(bromomethyl)phenoxyacetate or 4-(bromomethyl)phenoxyacetate.

The compounds of Formula XIX and Formula XX have pharmacological and pharmaceutical properties similar to those of Formula I and II compounds. In vitro inhibition of human platelet aggregation test result for the compounds of Examples 41–44 are given hereinafter.

TABLE IV

Inhibition of Human Platelet Aggregation of Formula XIX and XX Compounds

| Example | vs. ADP mcg/mL | % Inhibition |
| --- | --- | --- |
| 41 | 32 | 19 |
| 42 | 3 | 50 |
| 43 | 2 | 50 |
| 44 | 4 | 50 |

EXAMPLE 41

Methyl 8-[(4,5-diphenyl-2-oxazolyl)thio]octanoate

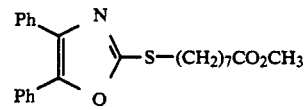

Sodium hydride (0.71 g of a 60% disp., 18 mmol) was added to a stirred solution of 4,5-diphenyl-2(3H)oxazolethione (4.05 g, 16 mmol) in dimethylformamide (50 ml) maintained under a nitrogen atmosphere. The mixture was stirred at room temperature for 15 minutes to give a suspension and methyl 8-bromooctanoate (3.83 g, 16 mmol) in DMF (10 mL) added dropwise. After the addition was complete, the reaction mixture was stirred at ambient temperature for 2.5 hours and at 50° C. for 30 minutes. The reaction mixture was diluted with Et$_2$O and H$_2$O and stirred. The organic layer was separated, dried (MgSO$_4$) and concentrated to leave an oil which was chromatographed on a column of silica gel. Elution with a mixture of hexanes and diethyl ether (initially 2:1, then 1:1 and finally 1:2) gave methyl 8-[(4,5-diphenyl-2-oxazolyl)thio]octanoate (4.40 g, 67.2%) as a partial hydrate.

Anal. Calcd. for $C_{24}H_{27}NO_3S$. 0.3 H$_2$O: C, 69.46; H, 6.70; N, 3.38, Found: C, 69.48; H, 6.88; N, 3.15.

$^1$H-NMR: (CDCl$_3$) delta: 1.26 to 2.33 (10H, m,), 2.30 (2H, t,), 3.24 (2H, t,), 3.66 (3H, s,), 7.31 (6H, m,) and 7.60 (4H, m,).

EXAMPLE 42

8-[(4,5-Diphenyl-2-oxazolyl)thio]octanoic Acid

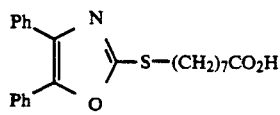

Methyl 8-[(4,5-diphenyl-2-oxazolyl)thio]octanoate (2.0 g, 4.9 mol) was dissolved in methanol (30 mL). A solution of lithium hydroxide monohydrate (0.41 g, 9.8 mmol) in water (8 mL) was added and the mixture heated to reflux for 1 hour. After cooling to room temperature, the methanol was removed in vacuo, the residue diluted with water and acidified to about pH 2 using dilute hydrochloric acid solution. The mixture was extracted with EtOAc, the combined extracts dried over MgSO$_4$ and concentrated. The residue was chromatographed on a column of silica gel using CH$_2$Cl$_2$/MeOH (95/5) as eluent to give 8-[(4,5-diphenyl-2-oxazolyl)thio]octanoic acid (1.70 g, 88%).

Anal. Calcd. for C$_{23}$H$_{25}$NO$_3$S. 0.4 H$_2$O: C, 68.59; H, 6.46; N, 3.48. Found: C, 68.84; H, 6.57; N, 3.23.

$^1$H-NMR (CDCl$_3$) delta: 1.27–1.80 (10H, m), 2.26 (2H, t), 3.18 (2H, t), 7.26 (6H, m) and 7.48 (4H, m).

EXAMPLE 43

Methyl [3-[[(4,5-Diphenyl-2-oxazolyl)thio]methyl]phenoxy]acetate

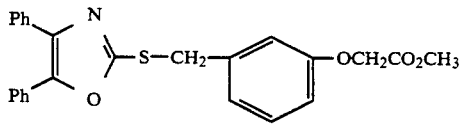

4,5-Diphenyl-2(3H)-oxazolethione (5.7 g, 22.8 mmol) was dissolved in DMF (100 mL). Sodium hydride (1.0 g of a 60% dispersion, 25 mmol) was added and the mixture stirred under a nitrogen atmosphere for 30 minutes. The clear solution was cooled to 0° C. and a solution of methyl 3-(bromomethyl)phenoxy acetate (6.5 g, 25 mmol) in DMF (10 mL) added dropwise. After the addition was complete, the suspension was stirred at 0° C. for 1 hour and then at room temperature for 2 hours. The reaction mixture was diluted with Et$_2$O and water (200 mL each) and stirred. The organic layer was separated, washed with wter (2×20 mL), dried (MgSO$_4$) and concentrated in vacuo. The crude material was purified by flash chromatography on silica gel using a mixture of hexane and diethyl ether (2:1) as eluent to give methyl [3-[[(4,5-diphenyl-2-oxazolyl)thio]methyl]phenoxy]acetate (1.5 g, 13%) as an oil.

Anal. Calcd. for C$_{25}$H$_{21}$NO$_4$S: C, 68.75; H, 4.69; N, 3.62. Found: C, 68.39; H, 4.65; N, 3.58.

$^1$H-NMR (CDCl$_3$) delta: 3.75 (3H, s), 4.40 (2H, s), 4.56 (2H, s), 6.78 (1H, dd, J=8 Hz, J'=2.5 Hz) and 6.98–7.92 (13H, m).

EXAMPLE 44

[3-[[(4,5-Diphenyl-2-oxazolyl)-thio]methyl]phenoxy]acetic Acid

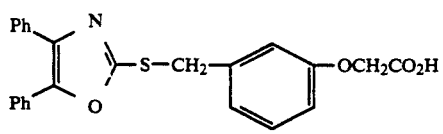

Methyl [3-[[(4,5-diphenyl-2-oxazolyl)thio]methyl]phenoxy]acetate (1.1 g, 2.6 mmol) was dissolved in methanol (25 mL). Lithium hydroxide monohydrate (0.22 g, 5.1 mmol) was added followed by the dropwise addition of water (5 mL). This mixture was heated at reflux for 30 minutes, cooled to room temperature and concentrated in vacuo. The residue was dissolved in water (15 mL) and acidified to about pH 2. The mixture was extracted with methylene chloride (25 mL), the combined extracts dried over MgSO$_4$ and concentrated in vacuo. The residue was purified by chromatography on a column of silica gel using a mixture of CH$_2$Cl$_2$ and MEOH (95:5) as eluent to give [3-[[4,5-diphenyl-2-oxazolyl)thio]methyl]phenoxy]acetic acid (0.6 g, 56.4%), m.p. 136°–137° C.

Anal. Calcd. for C$_{24}$H$_{19}$NO$_4$S: C, 69.05; H, 4.59; N, 3.36. Found: C, 68.83; H, 4.64; N, 3.35.

$^1$H-NMR (CDCl$_3$) delta: 4.41 (2H, s), 4.61 (2H), 6.82 (1H, dd, J=8.2 Hz, J'=2 Hz) and 7.03–7.64 (13H, m).

What is claimed is:

1. A compound of Formula II

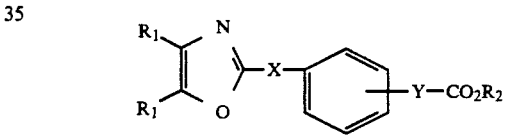

wherein

R$_1$ is phenyl or thienyl;

R$_2$ is hydrogen, lower alkyl or together with CO$_2$ is tetrazol-1-yl;

X is a divalent connecting group selected from the group consisting of CH$_2$CH$_2$, CH═CH, and CH$_2$O;

Y is a divalent connecting group attached to the 3 or 4 phenyl position selected from the group consisting of OCH$_2$, CH$_2$CH$_2$ and CH═CH.

2. The compound of claim 1 wherein R$_1$ is phenyl.

3. The compound of claim 1 wherein R$_1$ is phenyl, X is CH$_2$CH$_2$ and Y is OCH$_2$.

4. The compound of claim 1 which is methyl 2-[3-[2-(4,5-diphenyl-2-oxazolyl)ethyl]phenoxy]acetate.

5. The compound of claim 1 which is 2-[3-[2-(4,5-diphenyl-2-oxazolyl)ethyl]phenoxy]acetic acid.

6. The sodium salt of 2-[3-[2-(2,5-diphenyl-2-oxazolyl)ethyl]phenoxy]acetic acid.

7. The compound of claim 1 which is methyl 2-[4-[2-(4,5-diphenyl-2-oxazolyl)ethyl]phenoxy]acetate.

8. The compound of claim 1 which is 2-[4-[2-(4,5-diphenyl-2-oxazolyl)ethyl]phenoxy]acetic acid.

9. The compound of claim 1 which is ethyl 3-[3-[2-(4,5-diphenyl-2-oxazolyl)ethyl]phenyl-2-propenoate.

10. The compound of claim 1 which is 3-(3-[2-(4,5-diphenyl-2-oxazolyl)ethyl]phenyl]-2-propenoic acid.

11. The compound of claim 1 which is ethyl 3-[2-(4,5-dlphenyl-2-oxazolyl)ethyl]benzenepropanoate.

12. The compound of claim which is 3-[2-(4,5-diphenyl-2-oxazolyl)ethyl]benzenepropanoic acid.

13. The compound of claim 1 which is methyl [3-[2-(4,5-diphenyl-2-oxazolyl)ethenyl]phenoxy]acetate.

14. The compound of claim 1 which is [3-[2-(4,5-diphenyl-2-oxazolyl)ethenyl]phenoxy]acetic acid.

15. The compound of claim 1 which is methyl [4-[2-(4,5-diphenyl-2-oxazolyl)ethenyl]phenoxy]acetate.

16. The compound of claim 1 which is [4-[2-(4,5-diphenyl-2-oxazolyl)ethenyl]phenoxy]acetic acid.

17. The compound of claim 1 which is methyl 3-[3-[(4,5-diphenyl-2-oxazolyl)methoxy]phenyl]propanoate.

18. The compound of claim 1 which is 3-[3-[(4,5-diphenyl-2-oxazolyl)methoxy]phenyl)]propanoic acid.

19. The compound of claim 1 which is methyl 3-[4-[(4,5-diphenyl-2-oxazolyl)methoxy]phenyl]propanoate.

20. The compound of claim 1 which is 3-[4-[(4,5-diphenyl-2-oxazolyl)methoxy]phenyl]propanoic acid.

21. The compound of claim 1 which is methyl 3-[3-[(4,5-diphenyl-2-oxazolyl)methoxy]phenyl]-2-propenoate.

22. The compound of claim 1 which is 3-[3-[(4,5-diphenyl-2-oxazolyl)methoxy]phenyl]-2-propenoic acid.

23. The compound of claim 1 which is methyl 3-[4-[(4,5-diphenyl-2-oxazolyl)methoxy]phenyl]-2-propenoate.

24. The compound of claim 1 which is 3-[4-(4,5-diphenyl-2-oxazolyl)methoxy]phenyl]-2-propenoic acid.

25. The compound of claim 1 which is methyl 3-[(4,5-diphenyl-2-oxazolyl)methoxy]phenoxy]acetate.

26. The compound of claim 1 which is [3-[(4,5-diphenyl-2-oxazolyl)methoxy]phenoxy]acetic acid.

27. The compound of claim 1 which is ethyl 3-[3-[2-(4,5-diphenyl-2-oxazolyl)ethenyl]phenyl]-2-propenoate.

28. The compound of claim 1 which is methyl [3-[2-[4,5-di(3-thienyl)-2-oxazolyl]ethyl]phenoxy]acetate.

29. The compound of claim 1 which is [3-[2-[4,5di(3-thienyl)-2-oxazolyl]ethyl]phenoxy]acetic acid.

30. The compound of claim 1 which is methyl [3-[2-[4,5-di(2-thienyl)-2-oxazolyl]ethyl]phenoxy]acetate.

31. The compound of claim 1 which is [3-[2-[4,5-di(2-thienyl)-2-oxazolyl]ethyl]phenoxyacetic acid.

32. The compound of claim 1 which is 5-[[3-[2-(4,5-Diphenyl-2-oxazolyl)ethyl]phenoxy]methyl-1H-tetrazole.

33. The pharmaceutical composition comprising an aggregation inhibitory effective amount of a compound of claim 1 and a pharmaceutical carrier.

34. The method for inhibiting blood platelet aggregration in a mammal which comprises administering an aggregation inhibiting effective amount of a compound of claim 1.

* * * * *